(12) United States Patent
Park et al.

(10) Patent No.: US 9,745,605 B2
(45) Date of Patent: Aug. 29, 2017

(54) METHOD FOR PRODUCING MEDIUM-CHAIN ω-HYDROXY FATTY ACIDS, α,ω-DICARBOXYLIC ACIDS, AND ω-AMINO FATTY ACIDS FROM LONG-CHAIN FATTY ACIDS BY BIOTRANSFORMATION

(71) Applicant: EWHA UNIVERSITY-INDUSTRY COLLABORATION FOUNDATION, Seoul (KR)

(72) Inventors: Jin Byung Park, Seoul (KR); Ji Won Song, Seoul (KR); Eun Yeong Jeon, Iksan (KR)

(73) Assignee: EHWA UNIVERSITY-INDUSTRY COLLABORATION, Seoul (KR)

( * ) Notice: Subject to any disclaimer, the term of this patent is extended or adjusted under 35 U.S.C. 154(b) by 0 days.

(21) Appl. No.: 14/390,768

(22) PCT Filed: Apr. 5, 2013

(86) PCT No.: PCT/KR2013/002885
§ 371 (c)(1),
(2) Date: Oct. 3, 2014

(87) PCT Pub. No.: WO2013/151393
PCT Pub. Date: Oct. 10, 2013

(65) Prior Publication Data
US 2015/0057461 A1    Feb. 26, 2015

(30) Foreign Application Priority Data

Apr. 6, 2012   (KR) .................. 10-2012-0036372
May 25, 2012  (KR) .................. 10-2012-0056029
Jan. 18, 2013  (KR) .................. 10-2013-0005814

(51) Int. Cl.
| | | |
|---|---|---|
| A61K 49/04 | (2006.01) |
| C12P 13/00 | (2006.01) |
| C12P 7/64 | (2006.01) |
| C12P 7/46 | (2006.01) |
| C12P 7/02 | (2006.01) |
| C12P 7/04 | (2006.01) |
| C12N 1/20 | (2006.01) |
| C12N 1/00 | (2006.01) |
| C12N 9/02 | (2006.01) |
| C12P 7/44 | (2006.01) |
| C07C 59/01 | (2006.01) |
| C12N 15/52 | (2006.01) |
| C12P 7/62 | (2006.01) |

(52) U.S. Cl.
CPC ............ *C12P 7/6409* (2013.01); *C07C 59/01* (2013.01); *C12N 9/0073* (2013.01); *C12N 15/52* (2013.01); *C12P 7/04* (2013.01); *C12P 7/44* (2013.01); *C12P 7/62* (2013.01); *C12P 7/6436* (2013.01); *Y02E 50/17* (2013.01)

(58) Field of Classification Search
CPC ......... C12N 15/52; C12N 9/0073; C12P 7/62; C12P 7/6436; C12P 7/6409; C12P 7/04; C12P 7/44; C07C 59/01; Y02E 50/17
USPC ........ 554/219; 435/128, 134, 145, 155, 157, 435/252.3, 254.11
See application file for complete search history.

(56) References Cited

U.S. PATENT DOCUMENTS

| | | |
|---|---|---|
| 5,420,316 A | 5/1995 | Rebrovic |
| 5,952,517 A | 9/1999 | Ries et al. |
| 6,392,074 B1 | 5/2002 | Logan et al. |
| 2010/0285545 A1 | 11/2010 | Gross et al. |
| 2011/0105774 A1 | 5/2011 | Dubois |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Diefenbach et al., Synthesis of trans unsaturated fatty acids in Pseudomonas putida P8 by direct isomrerization of the double bond of lipid. Arch Microbiol., 1994, vol. 162: 120-125.*
Kisselev L., Polypeptide release factors in prokaryotes and eukaryotes: same function, different structure. Structure, 2002, vol. 10: 8-9.*
Godard et al., New environmentally friendly oxidative scission of oleic acid into azelaic acid and pelargonic acid. J Am Oil Cem Soc., 2013, vol. 90: 133-140.*

(Continued)

*Primary Examiner* — Ganapathirama Raghu
(74) *Attorney, Agent, or Firm* — Abel Law Group, LLP

(57) ABSTRACT

The present invention relates to a transformant which is transformed to express Baeyer-Villiger monooxygenase (BVMO), a method for producing C5-C14 medium-chain ω-hydroxy fatty acids, α,ω-dicarboxylic acids, ω-amino fatty acids, or alcohols from C16-C20 long-chain fatty acids by biotransformation using the transformant, a method for producing a fatty acid derivative having an ester group which is introduced into the chain thereof from keto fatty acid using the BVMO, and novel ω-hydroxy fatty acids which are prepared by the method. Degradation products such as C5 to C14 ω-hydroxy fatty acids, α,ω-dicarboxylic acids, ω-amino fatty acids, alcohols can be produced in a large amount from C16 to C20 long-chain fatty acids contained in a medium by biotransformation using a transformant capable of expressing BVMO of the present invention. Therefore, it can be widely used to produce ω-hydroxy fatty acids, α,ω-dicarboxylic acids, ω-amino fatty acids or alcohols in a more safe and economic manner.

15 Claims, 15 Drawing Sheets

(56) References Cited

OTHER PUBLICATIONS

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Stepanou E.G., a, o-Dicarboxylic acid salts and a,o-Dicarboxylic acids. Naturwissenschaften, 1992, vol. 79: 128-131.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Aliphatic compound: Six (6) pages downloaded from https://en.wikipedia.org/wiki/Lactone on Jul. 7, 2016.*

Fatty acid: Seven (7) pages downloaded from https://en.wikipedia.org/wiki/Fatty acid on Jul. 5, 2016.*

Lactone: Six (6) pages downloaded from https://en.wikipedia.org/wiki/Lactone on Jul. 5, 2016.*

Joo et al., Production of 10-hydroxystearic acid from oleic acid by whole cells of recombinant *Escherichia coli* containing oleate hydratase from Stenotrophomonas maltophilia. J. Biotechnol., 2012, vol. 158: 17-23.*

Kellerhals et al., Renewable long-chain fatty acids for production of biodegradable medium-chain-length polyhydroxyalkanoates (mcl-PHAs) at laboratory and pilot plant scales. Macromolecules, 2000, vol. 33: 4690-4698.*

Rehdorf et al., Cloning, expression and characterization of a Baeyer-Villiger monooxygenase from Pseudomonas putida KT2440, Biotechnol Lett, May 26, 2007, 29:1393-1398.

J. Chem, Soc., 1963, pp. 5889-5893.

Eur. J. Org. Chem., 2002, pp. 3711-3730.

Biochem. Lett., 2007, vol. 29, pp. 1393-1398.

Applied Microbiology and Biotechnology, 2009, vol. 85, pp. 13-25.

Angewandte Chemie International Edition, Jan. 30, 2013, vol. 52, pp. 2534-2537.

EBI Seminar Series Seminar Abstract, Feb. 12, 2013, p. 1.

Frontiers in Microbiology, Mar. 2013, vol. 4, pp. 1-13.

Extended European Search Report for PCT/KR2013002885 mailed Sep. 25, 2015.

The Journal of Biological Chemistry, vol. 279(5), Issue of Jan. 30, pp. 3354-3360 (2004).

Hildebrandt et al., Cloning, functional expression and biochemical characterization of a stereoselective alcohol dehydrogenase from Pseudomonas fluorescens DSM50106, Appl Microbiol Biotechnol, Jun. 26, 2002, 59:483-487.

Kirschner et al., Design of a secondary alcohol degradation pathway from Pseudomonas fluorescens DSM 50106 in an engineered *Escherichia coli*, Appl Microbiol Biotechnol, Mar. 9, 2007, 75:1095-1101.

Kirschner et al., Cloning, expression, and characterization of a Baeyer-Villiger monooxygenase from Pseudomonas fluorescens DSM 50106 in *E. coli*, Applied Microbiology and Biotechnology, published online Aug. 31, 2006, vol. 73, No. 5, p. 1065-1072.

Beilen et al., Cloning of Baeyer-Villiger monooxygenases from Comamonas, Xanthobacter and Rhodococcus using polymerase chain reaction with highly degenerate primers, Environmental Microbiology, 2003, 5(3), p. 174-182.

\* cited by examiner

[FIG. 1a]
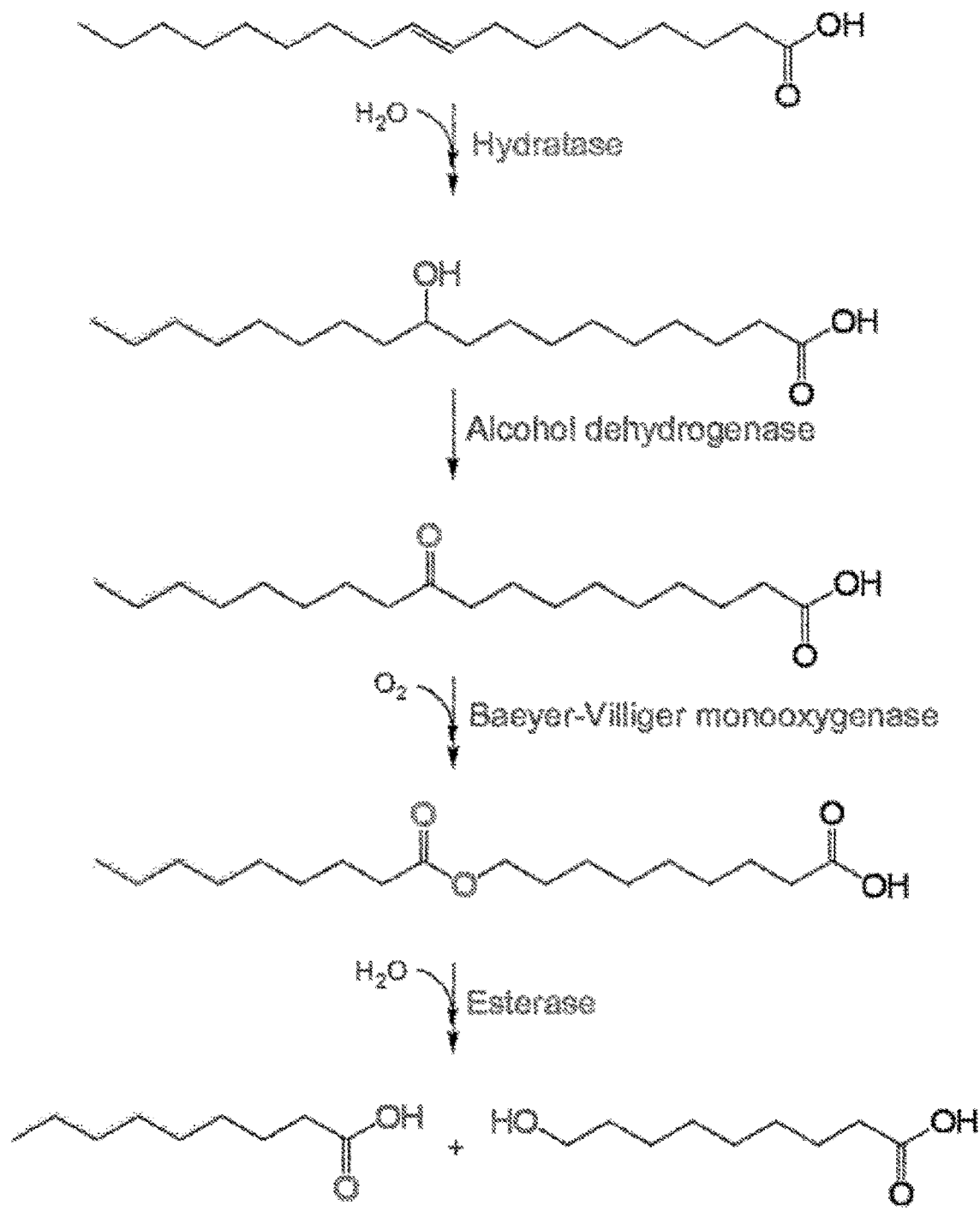

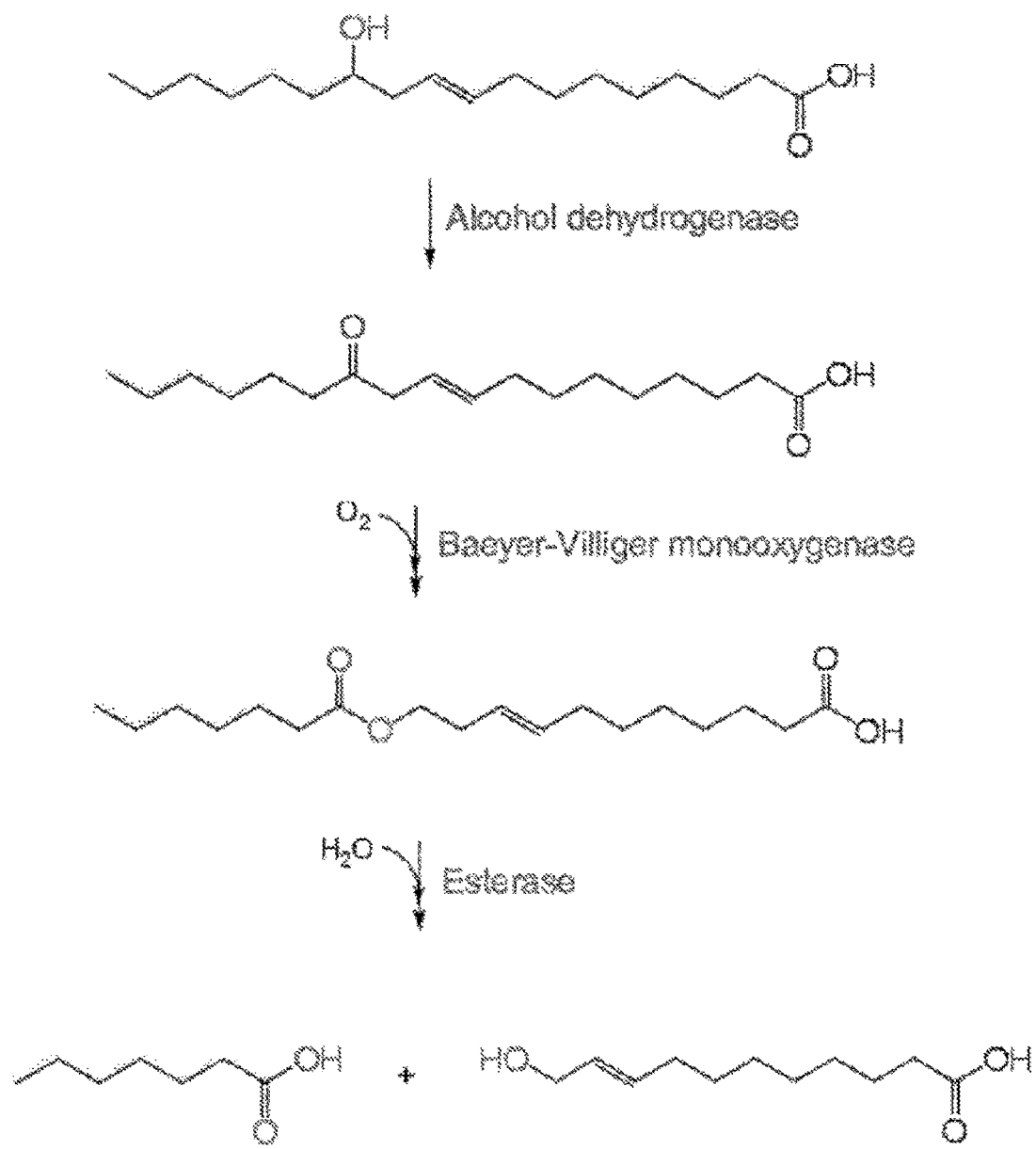
[FIG. 1b]

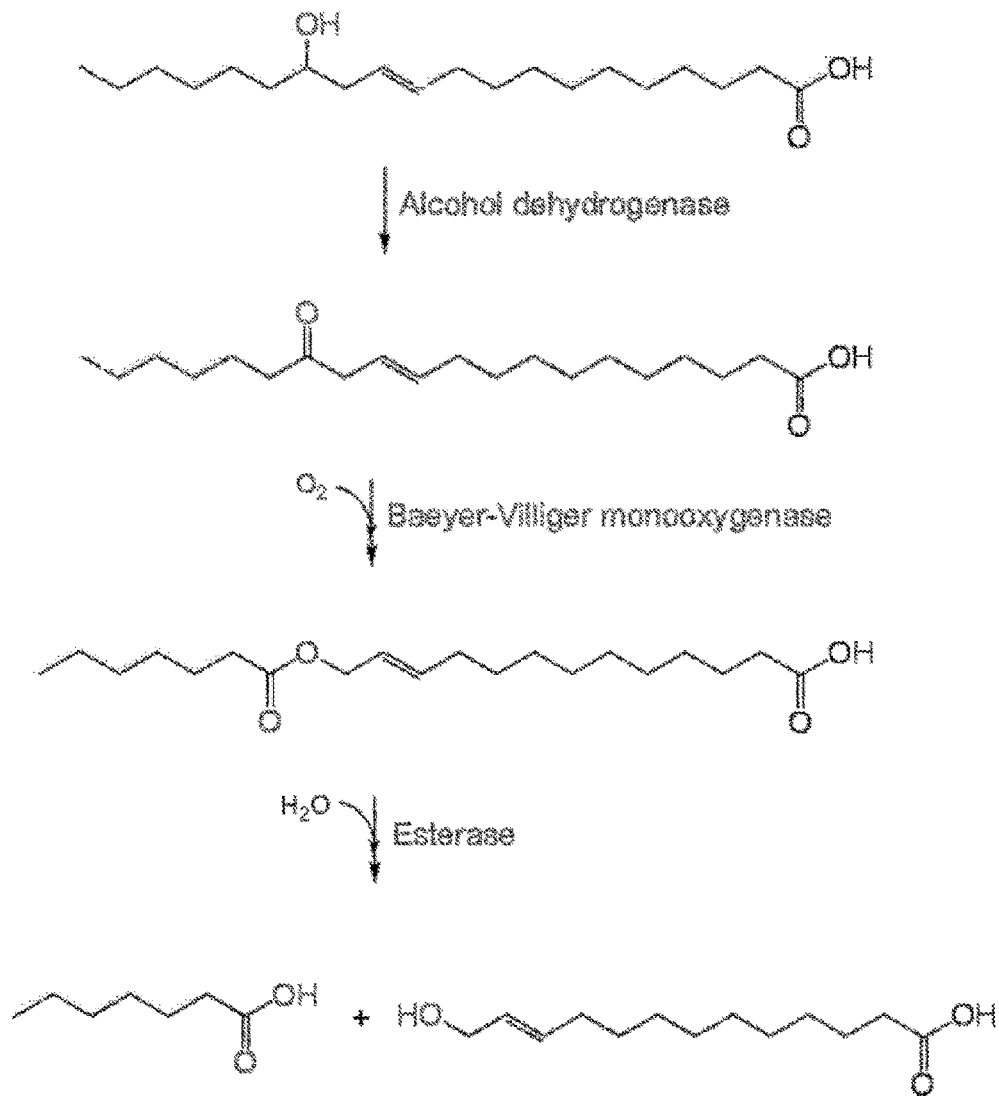
[FIG. 1c]

[FIG. 1d]
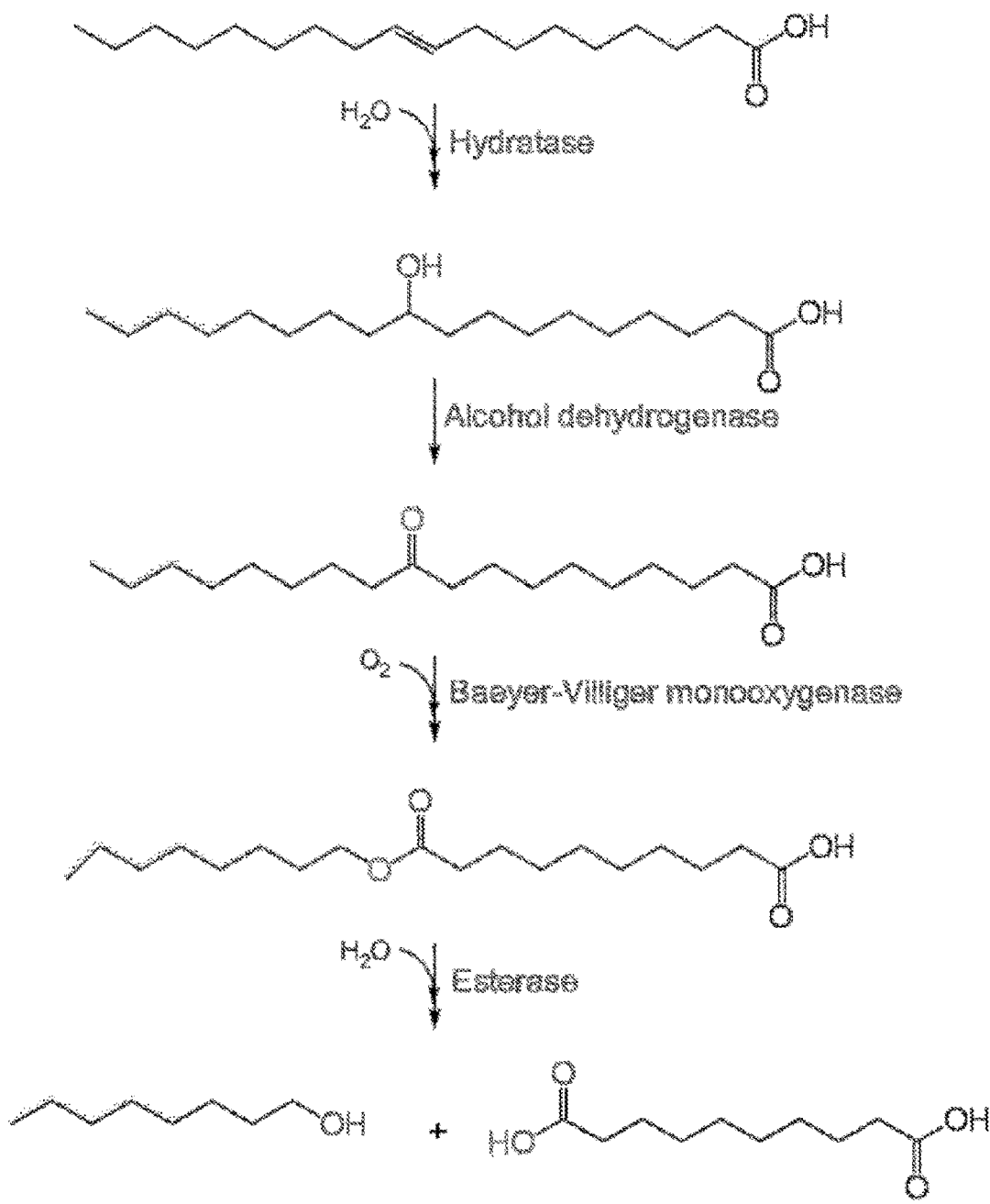

[FIG. 1e]
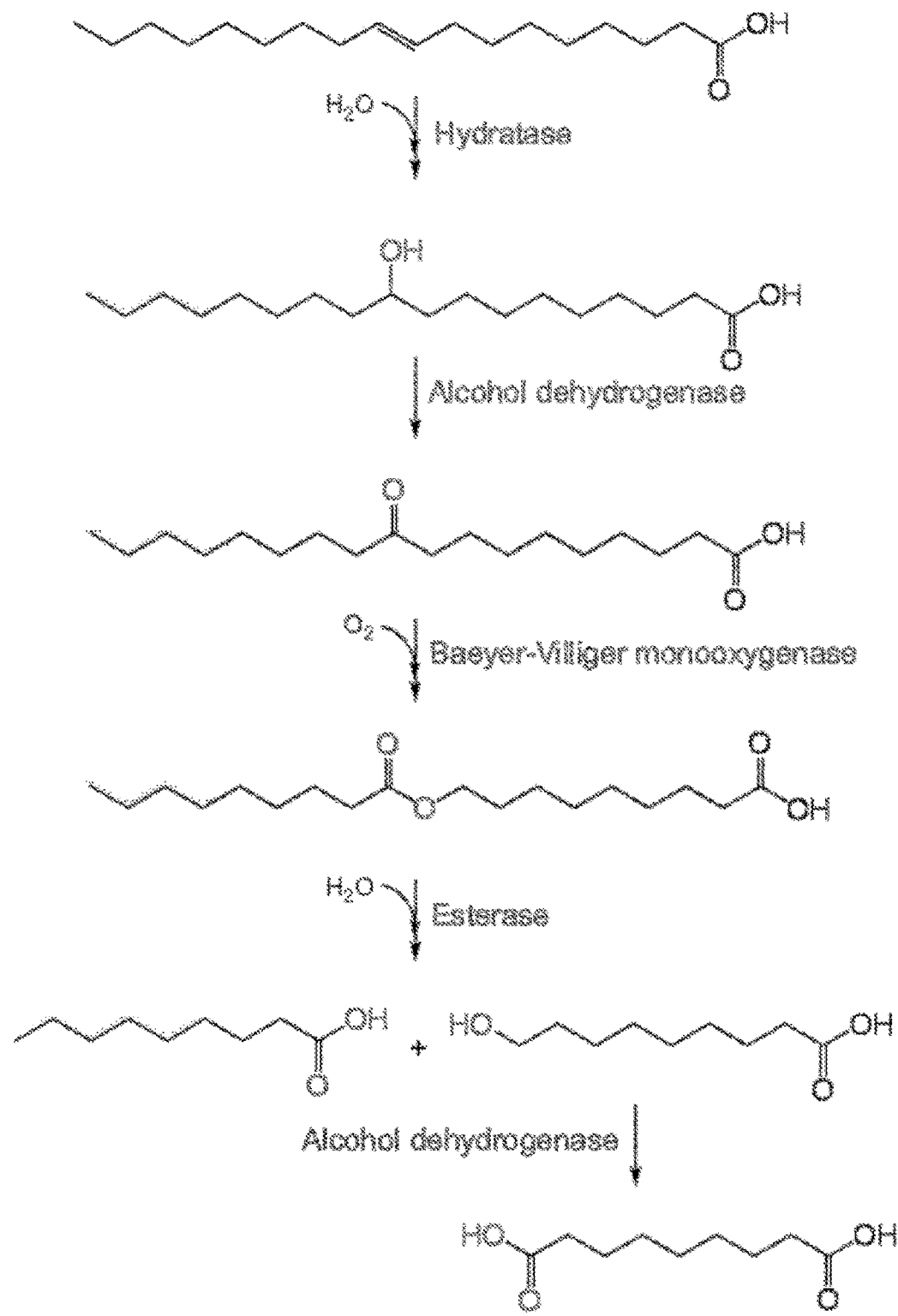

[FIG. 1f]
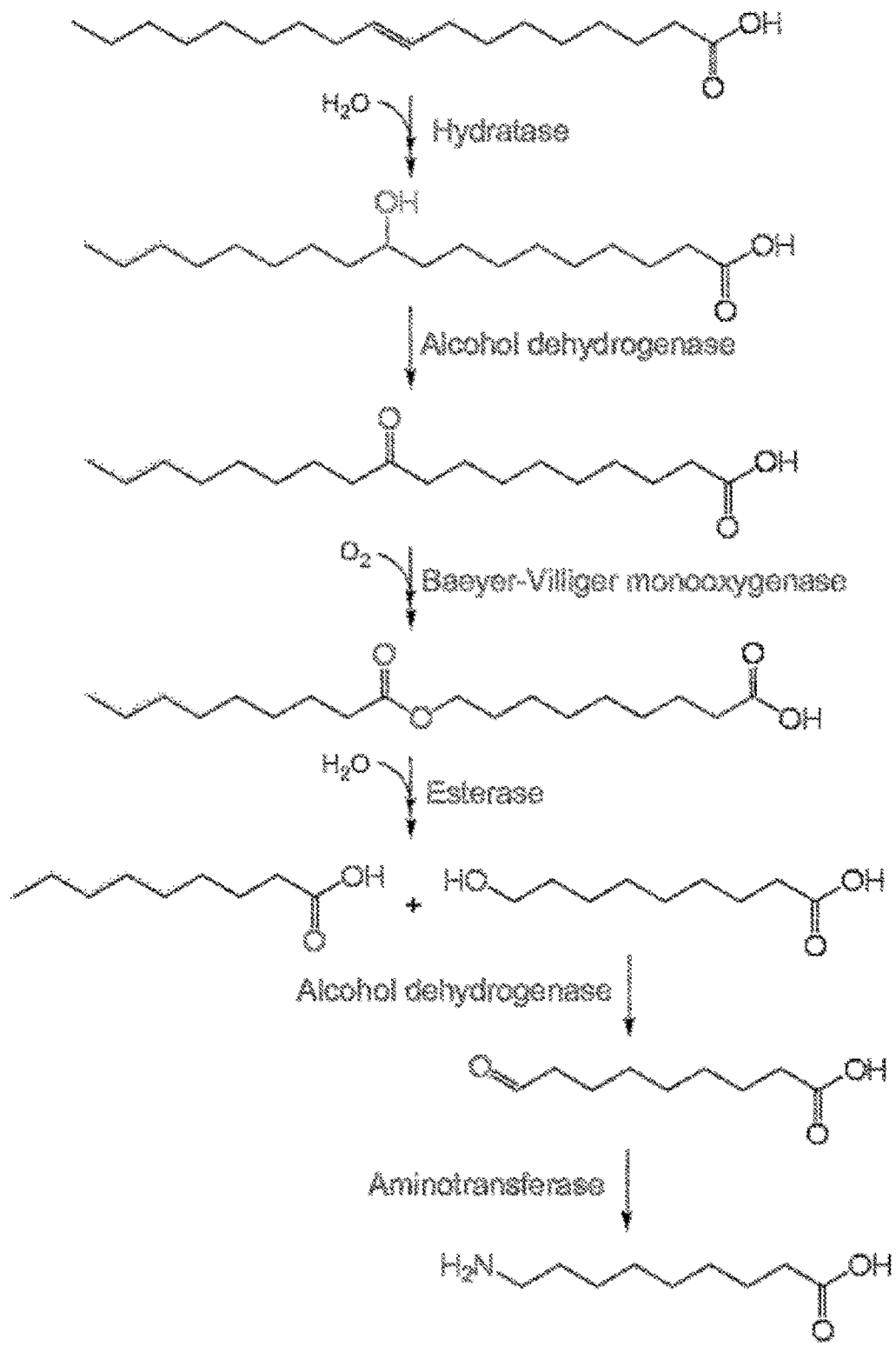

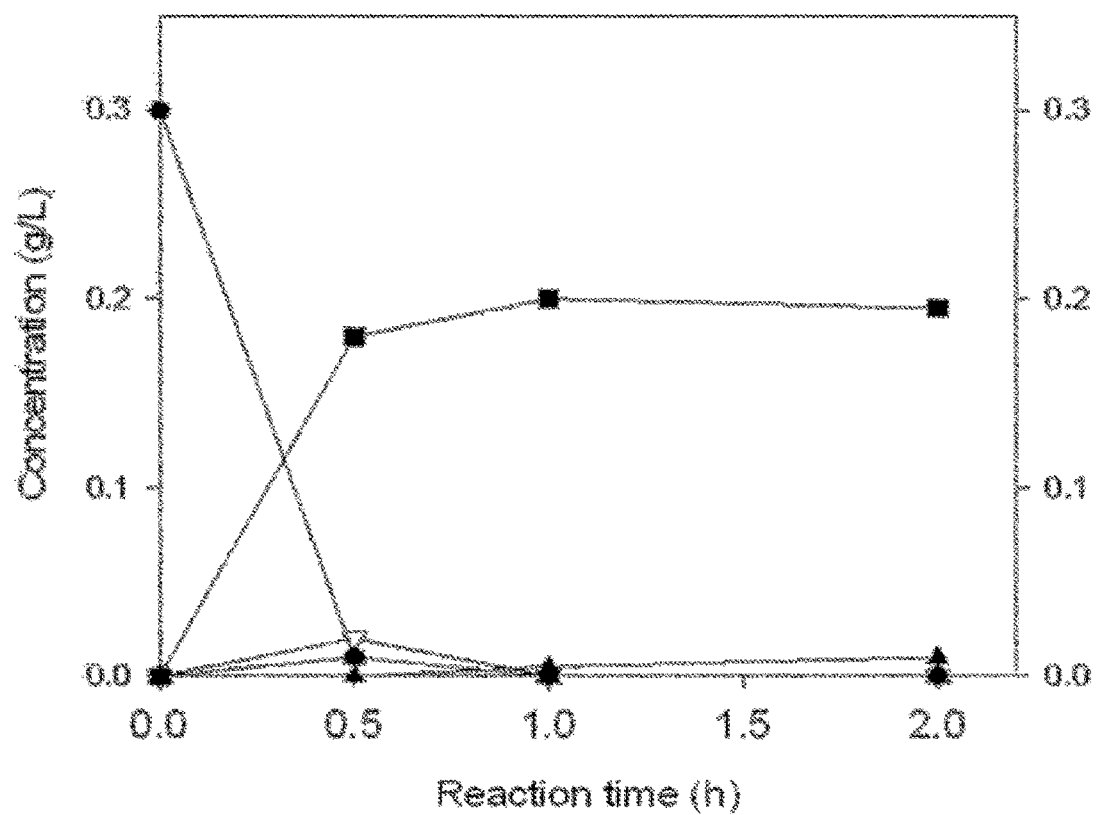
[FIG. 2a]

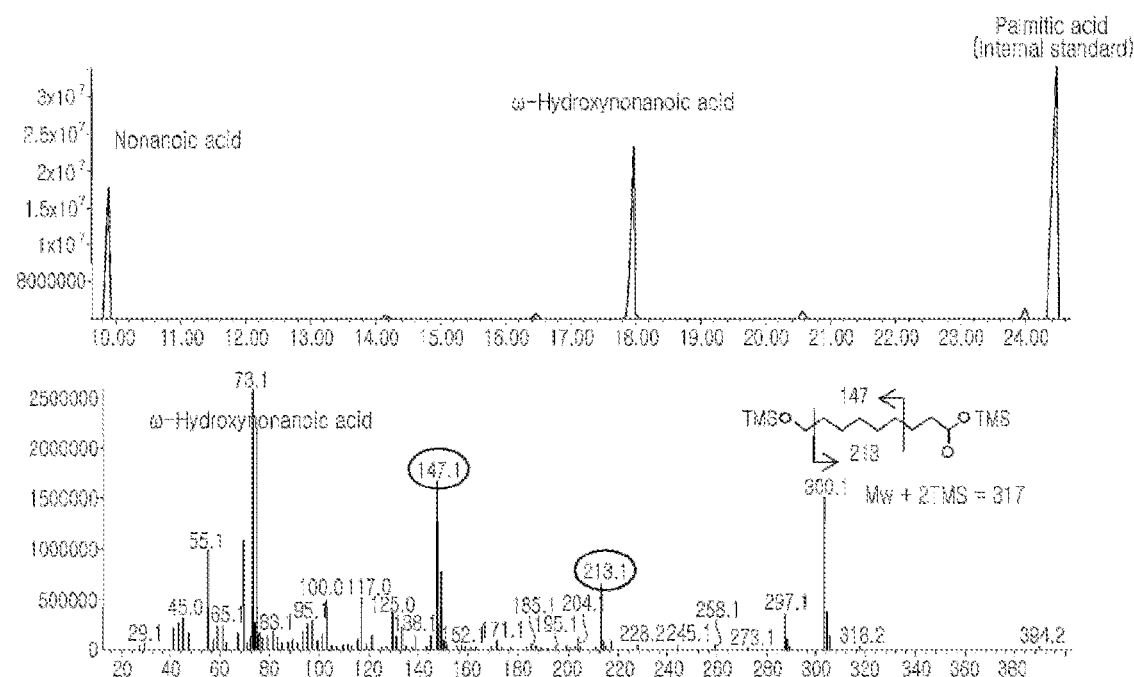
[FIG. 2b]

[FIG. 3a]
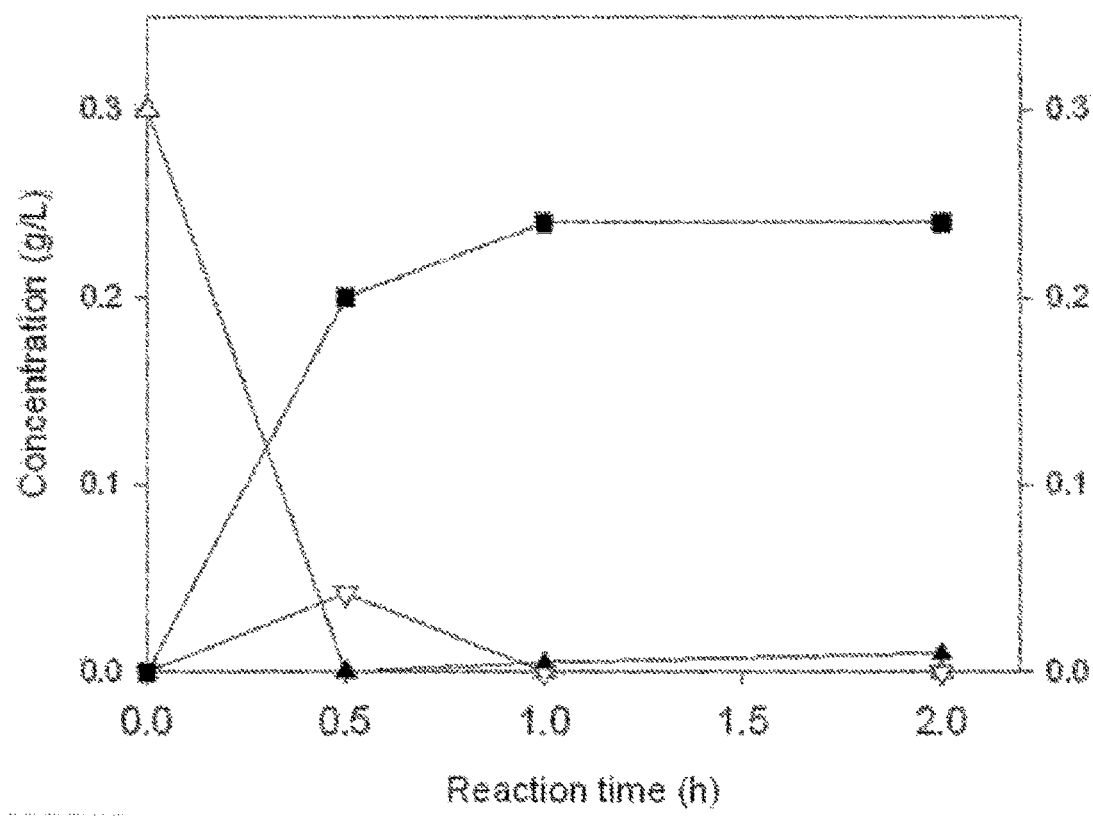

[FIG. 3b]
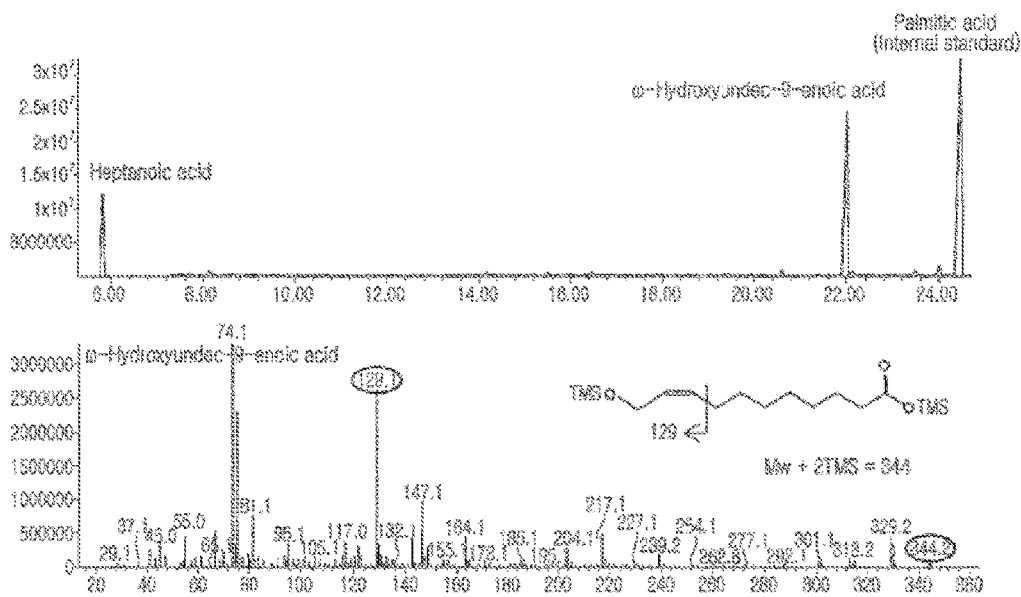
[FIG. 4]
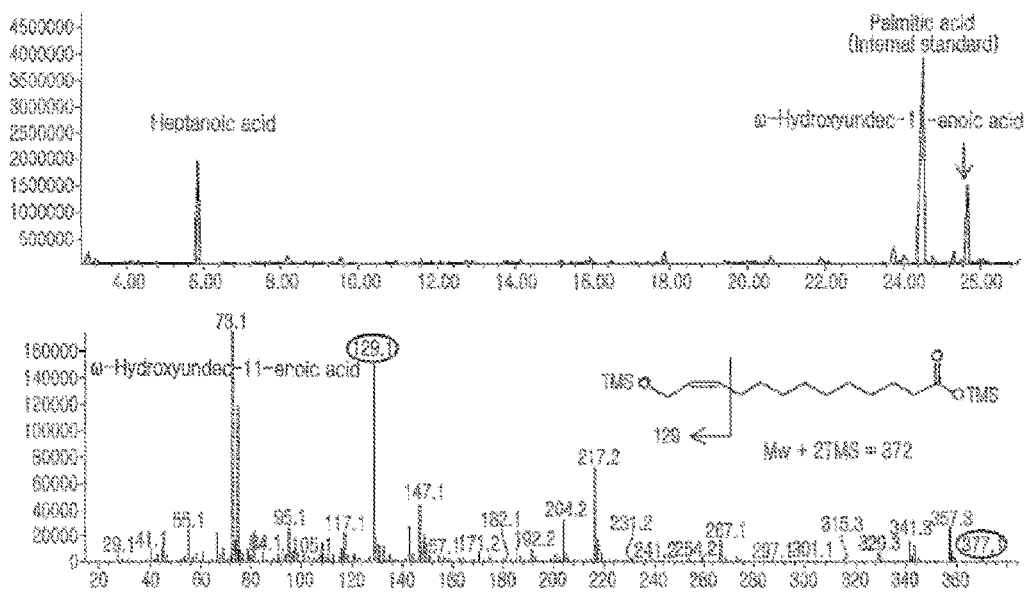

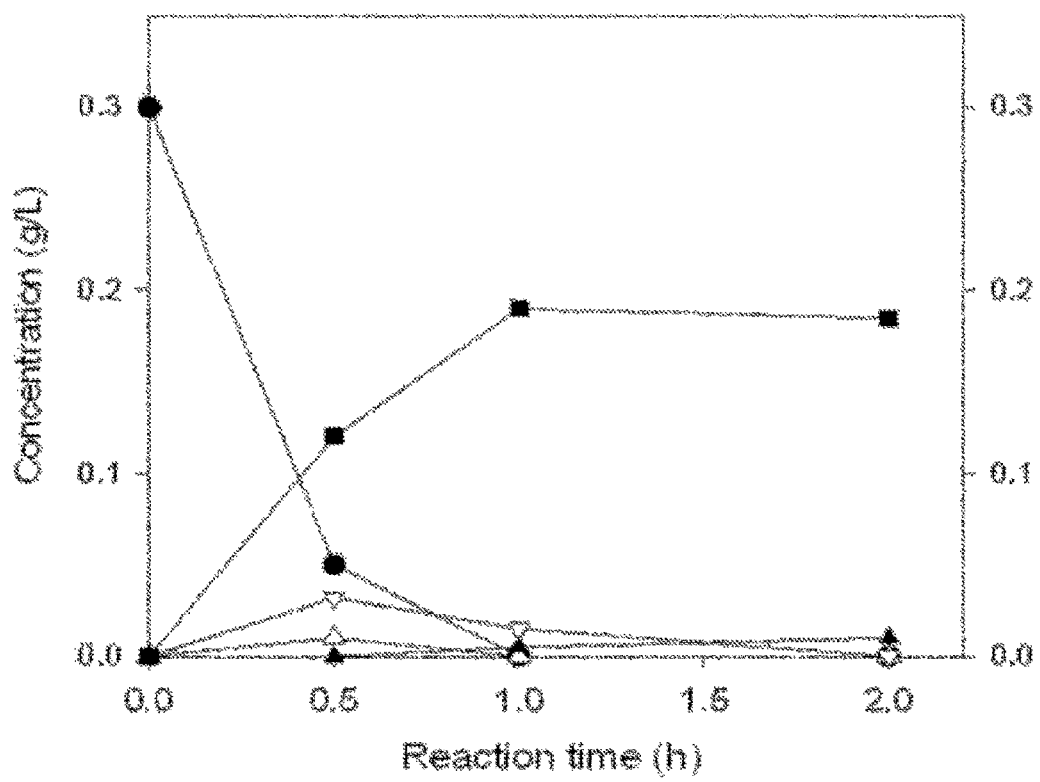
[FIG. 5a]

[FIG. 5b]
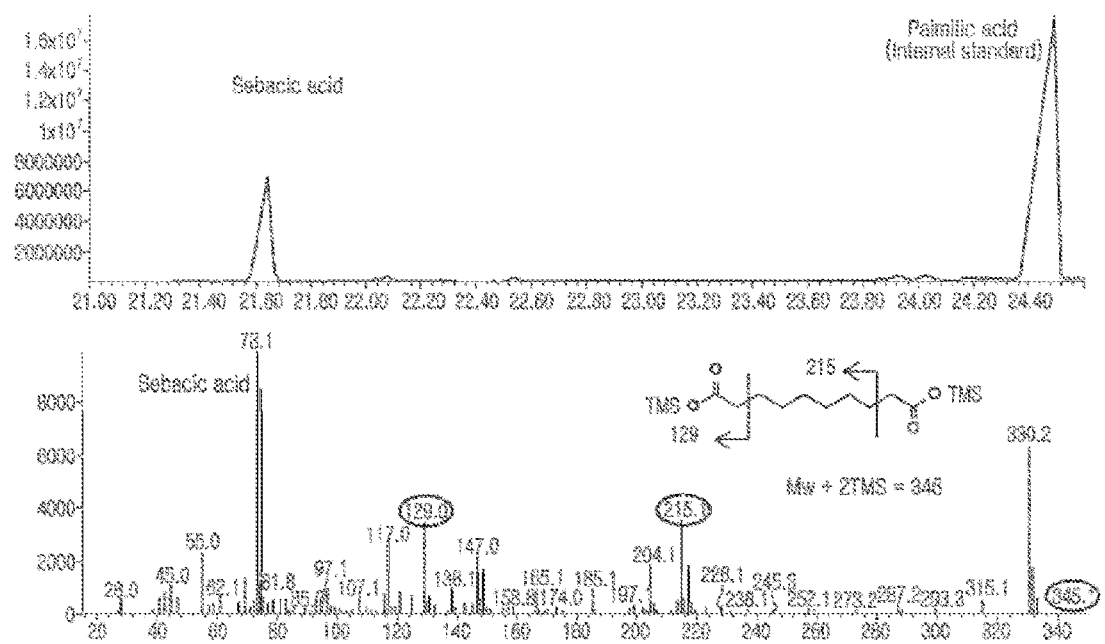

[FIG. 6]
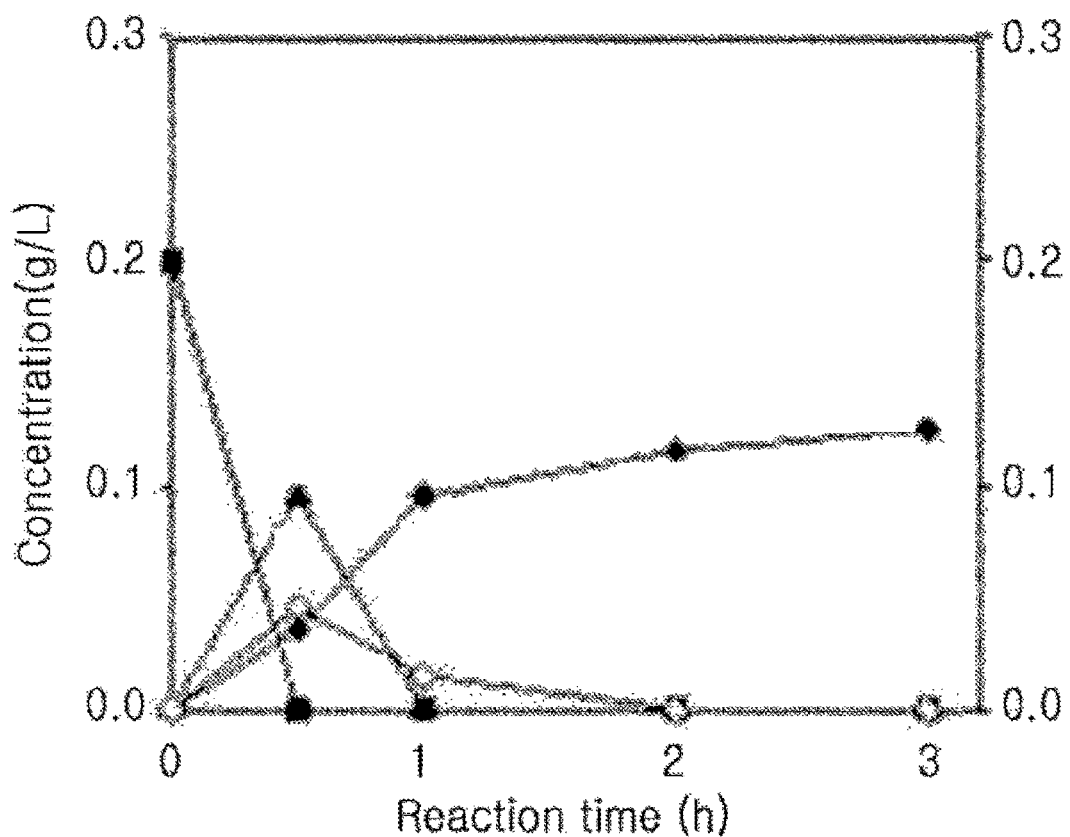

[FIG. 7]
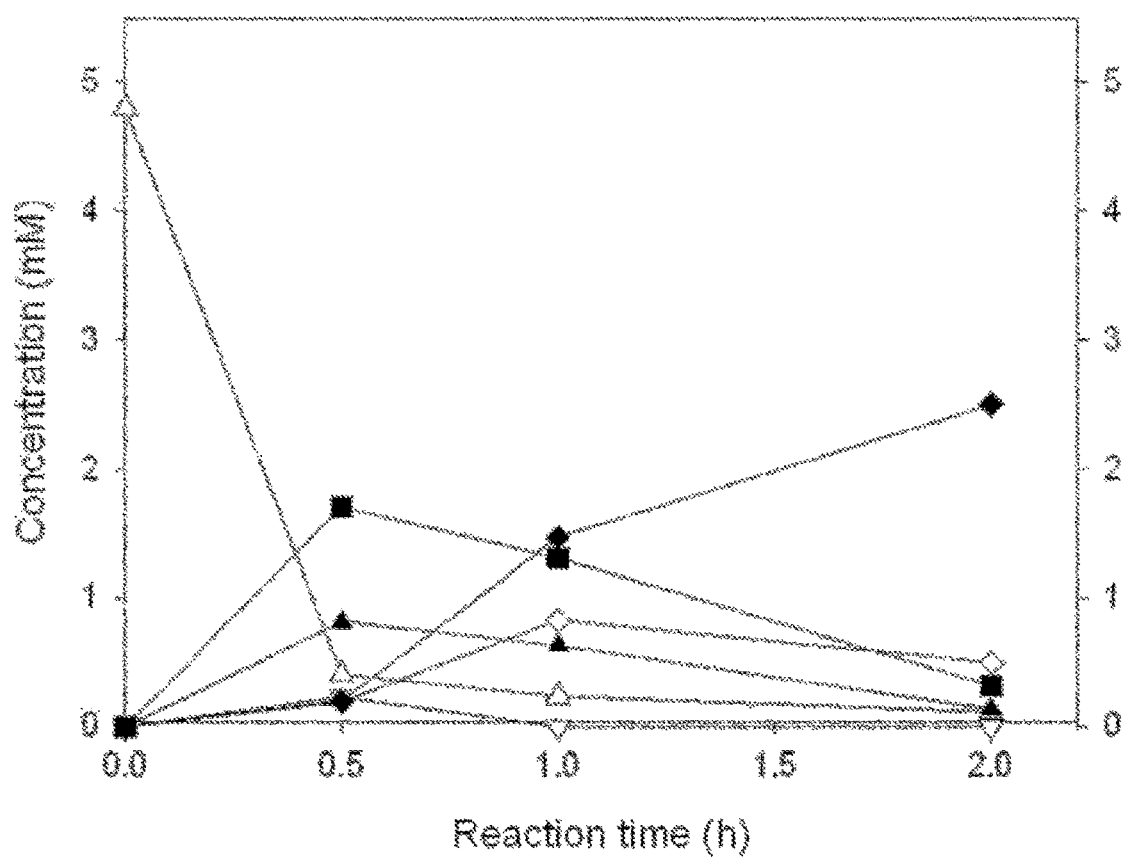

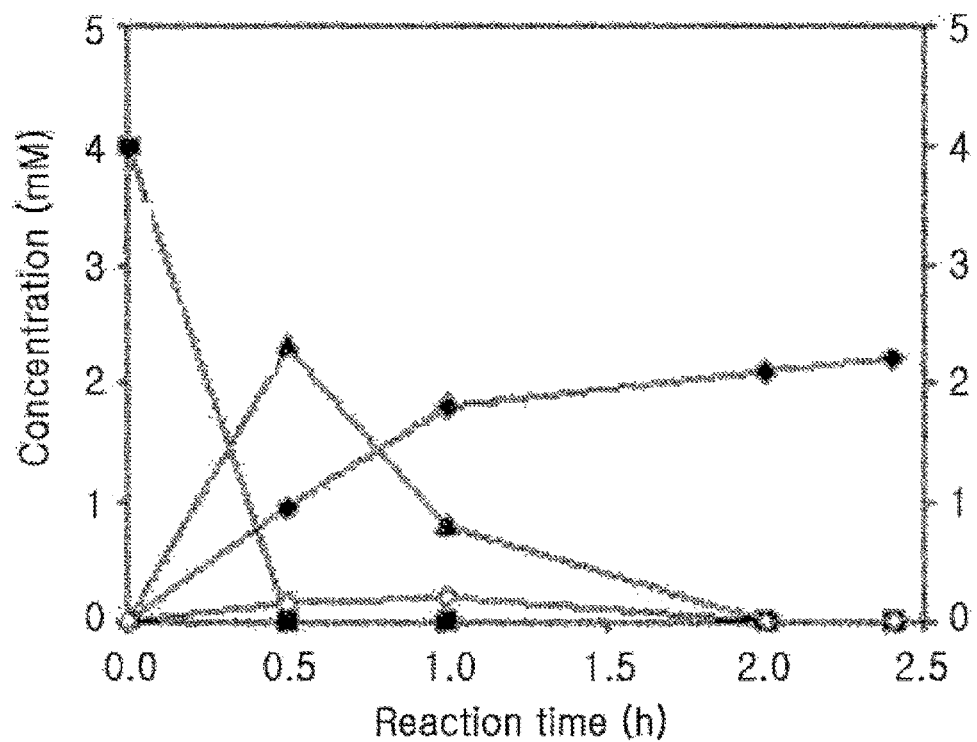
[FIG. 8]

SEQUENCE LISTING

```
<160> NUMBER OF SEQ ID NOS: 9

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctagcatgt attacagtaa tggtaactat gaa                                  33

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggctcgagct atattagttt actttctttc a                                    31

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcgaattcg tccgagttca cccgtttcga                                      30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atatcaagct tcagccgagc ggggtgtcct                                      30

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 5
gcgccatatg atgagcacat ttgttgcaaa a                                      31

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgcctcgag tcagtggtga tggtgatgat gactccgccg ccacttt                     47

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcgcggatcc gatgtacgac tatataatcg tt                                     32

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgcgcggcc gcttagtggt gatggtgatg atgcatgcag acagctat                    48

<210> SEQ ID NO 9
<211> LENGTH: 546
<212> TYPE: PRT
<213> ORGANISM: Unknown
<220> FEATURE:
<223> OTHER INFORMATION: Description of Unknown: Bacteria polypeptide

<400> SEQUENCE: 9

Met Thr Glu Ala Val Thr Lys Ser Asn Gly His Asn Gly Thr His Val
1               5                   10                  15

Thr Ala Lys Leu Asp Ala Val Val Gly Ala Gly Val Ala Gly Leu
            20                  25                  30

Tyr Gln Leu Tyr Arg Leu Arg Glu Gln Gly Leu Thr Val Arg Ala Phe
        35                  40                  45

Asp Ala Ala Ser Gly Val Gly Gly Thr Trp Tyr Trp Asn Arg Tyr Pro
    50                  55                  60

Gly Ala Arg Phe Asp Ser Glu Ser Tyr Ile Tyr Gln Tyr Leu Phe Ser
65                  70                  75                  80

Glu Glu Leu Tyr Lys Gly Trp Ser Trp Ser Glu Arg Phe Pro Gly Gln
                85                  90                  95

Pro Glu Ile Glu Arg Trp Leu Asn Tyr Val Ala Asp Arg Leu Asp Leu
            100                 105                 110

Arg Lys Asp Ile Gln Phe Gly Thr Ala Ile Val Ser Ala His Phe Asp
        115                 120                 125

Asp Ala Thr Gln Arg Trp Arg Val Thr Thr Asp Gln Gly Asp Gly Val
    130                 135                 140

-continued

```
Asp Thr Gln Phe Ile Ile Thr Cys Cys Gly Met Leu Ser Ala Pro His
145                 150                 155                 160

Val Ser Phe Pro Gly Gln Asp Thr Phe Gly Gln Val Phe His Thr
            165                 170                 175

Ala Arg Trp Pro Ala Gln Pro Val Asp Phe Ala Gly Lys Arg Val Gly
            180                 185                 190

Ile Val Gly Asn Gly Ala Thr Gly Ile Gln Val Ile Gln Thr Ile Ala
            195                 200                 205

Ser Glu Val Gly His Leu Lys Val Phe Met Arg Thr Pro Gln Tyr Ile
    210                 215                 220

Ile Pro Met Lys Asn Pro Lys Tyr Gly Ala Ala Asp Ala Glu Ala Tyr
225                 230                 235                 240

Lys Ser Lys Phe Lys His Phe Val Glu Arg Leu Pro His Thr Phe Thr
                245                 250                 255

Gly Phe Glu Tyr Asp Phe Glu His Ala Trp Ala Ala Leu Thr Ala Glu
            260                 265                 270

Lys Arg Arg Glu Val Leu Glu Asp Cys Trp Asn Asp Gly Ser Leu Lys
            275                 280                 285

Leu Trp Ile Ser Ser Phe Ala Glu Leu Phe Phe Asp Asp Ala Val Asn
    290                 295                 300

Gly Glu Ile Ser Glu Phe Val Arg Glu Lys Met Arg Glu Arg Leu Lys
305                 310                 315                 320

Asp Pro Lys Leu Cys Asp Leu Leu Ile Pro Gln Asp Tyr Gly Phe Gly
                325                 330                 335

Thr His Arg Val Pro Leu Glu Gln Asn Phe Leu Glu Ala Phe His Arg
            340                 345                 350

Pro Asn Val Glu Ile Val Glu Val Lys Thr Asn Pro Ile Glu Cys Val
            355                 360                 365

Thr Arg Glu Gly Ile Gln Leu Ala Asp Gly Thr Val His Glu Leu Asp
    370                 375                 380

Ile Ile Ile Leu Ala Thr Gly Phe Asp Ala Gly Ser Gly Ala Leu Met
385                 390                 395                 400

Arg Ile Asp Ile Arg Gly Arg Gly Gly Arg Ser Leu Lys Asp Glu Trp
                405                 410                 415

Ser Arg Asp Ile Arg Thr Thr Met Gly Leu Gln Ile His Gly Tyr Pro
            420                 425                 430

Asn Leu Phe Thr Thr Ala Val Pro Leu Ala Pro Ser Ala Ala Leu Cys
            435                 440                 445

Asn Met Thr Thr Cys Leu Gln Gln Val Glu Trp Ile Asp Asp Cys
    450                 455                 460

Ile Arg Tyr Val Arg Ala Asn Ser Leu Ala Ala Val Glu Pro Thr Lys
465                 470                 475                 480

Glu Thr Gln Asp Ala Trp Val Ala His His Asp Glu Ile Ala Asn Ala
                485                 490                 495

Thr Leu Ile Ala Lys Thr Asn Ser Trp Tyr Leu Gly Ser Asn Val Lys
            500                 505                 510

Gly Lys Pro Arg Arg Val Leu Ser Tyr Cys Gly Gly Val Gly Ala Tyr
            515                 520                 525

Arg Gln Lys Cys Asp Glu Val Ala Ala Ser Gly Tyr Gln Gly Phe Ala
    530                 535                 540

Met Arg
545
```

US 9,745,605 B2

METHOD FOR PRODUCING MEDIUM-CHAIN ω-HYDROXY FATTY ACIDS, α,ω-DICARBOXYLIC ACIDS, AND ω-AMINO FATTY ACIDS FROM LONG-CHAIN FATTY ACIDS BY BIOTRANSFORMATION

SEQUENCE LISTING

The instant application contains a Sequence Listing which has been submitted electronically in ASCII format and is hereby incorporated by reference in its entirety. Said ASCII copy, created on Oct. 3, 2014, is named 1214-G001_SL.txt and is 7,137 bytes in size.

BACKGROUND OF THE INVENTION

1. Field of the Invention

The present invention relates to a method for producing medium-chain ω-hydroxy fatty acids, α,ω-dicarboxylic acids, and ω-amino fatty acids from long-chain fatty acids by biotransformation. More particularly, the present invention relates to a transformant which is transformed to express Baeyer-Villiger monooxygenase (BVMO), a method for producing C5-C14 medium-chain ω-hydroxy fatty acids, α,ω-dicarboxylic acids, ω-amino fatty acids, or alcohols from C16-C20 long-chain fatty acids by biotransformation using the transformant, a method for producing a fatty acid derivative having an ester group which is introduced into the chain thereof from keto fatty acid using the BVMO, and novel ω-hydroxy fatty acids which are prepared by the method.

2. Description of the Related Art

ω-hydroxy fatty acid is a fatty acid (HOCH$_2$(CH$_2$)$_n$COOH) with one hydroxyl group at the end of the fatty acid. It has been used as a monomer in the production of polyethylene-based plastics, and is widely used in the production of emulsifiers, adhesives, or coatings and in the preparation of cosmetics or medicines. ω-hydroxy fatty acid can be also used as a precursor in the synthesis of long-chain dicarboxylic acids which are widely used in the production of polyamide, polyester-based plastics, cosmetics and household items.

Medium-chain α,ω-dicarboxylic acid (HOOC(CH$_2$)$_n$COOH) and ω-amino fatty acid (H$_2$NCH$_2$(CH)$_n$COOH) have been used as monomers in the production of plastics of polyamide, polyester, etc., and also used in the production of emulsifiers, antifreezes, paints, and coatings. Further, they have a variety of physiological activities such as antibacterial activity, etc., and thus are widely used in the production of cosmetics, foods, and household items. For example, annual production capacity of a C10 medium-chain dicarboxylic acid, sebacic acid ((HOOC)(CH$_2$)$_8$(COOH)) is over 50,000 MT, and it is used in the production of plastics, candles, cosmetics, emulsifiers, antifreezes, and corrosion inhibitors. Further, sebacic acid is used in the production of acne treatments or cosmetics, and household items owing to its antibacterial activity.

Such medium-chain ω-hydroxy fatty acid, α,ω-dicarboxylic acid, and ω-amino fatty acid are rarely found in nature, and thus are industrially produced by chemical synthesis. Chemical synthesis has problems of requiring high temperature and high pressure, strong acids and/or toxic oxides causing severe environmental problems (U.S. Pat. Nos. 5,952,517, 6,392,074, 5,420,316, and 20110105774). For example, sebacic acid is produced from ricinoleic acid by chemical cleavage (U.S. Pat. Nos. 5,952,517 and 6,392,074). However, chemical cleavage of ricinoleic acid requires a high temperature process at 200-300° C. or higher and use of strong acids such as sulfuric acid and use of toxic substances such as a heavy metal ion catalyst, an organic solvent, etc. Problematically, this process is dangerous and produces a large amount of environmental pollutants after production.

Azelaic acid, a C9 medium-chain dicarboxylic acid, is produced by ozonolysis of oleic acid (U.S. Pat. No. 5,420,316). However, the production of azelaic acid by the above technique requires the use of a strong oxidizer ozone, which produces various by-products. Therefore, a separation/purification process using a heavy metal catalyst is essential to remove the by-products produced thereof. Due to many other problems including the complex separation/purification process, environmental pollution, and excessive energy use, there has been a growing need to study solutions of the problems. Accordingly, there has been an active study focused on a simple and environmentally friendly production method, and the use of a biocatalytic process in the method. For example, a method of producing long-chain ω-hydroxy fatty acids from long-chain fatty acids using enzymes and a production method of medium-chain dicarboxylic acids from a petroleum compound hydrocarbon have been developed. However, a method of producing medium-chain ω-hydroxy fatty acids, α,ω-dicarboxylic acids, ω-amino fatty acids, or alcohols from renewable long-chain fatty acids using enzymes has not been developed yet.

The present inventors newly demonstrated that BVMO is able to convert keto fatty acids derived from C16 to C20 long-chain fatty acids into fatty acid derivatives having an ester group introduced into the chain thereof, which can be cleaved by ester hydrolase, and they found that medium-chain ω-hydroxy fatty acids, α,ω-dicarboxylic acids, ω-amino fatty acids, alcohols, etc. can be produced from long-chain fatty acids using a transformed microorganism introduced with the BVMO gene, thereby completing the present invention.

SUMMARY OF THE INVENTION

An objective of the present invention is to provide a transformant capable of expressing BVMO.

Another objective of the present invention is to provide a method for producing various degradation products from long-chain fatty acids by biotransformation using the transformant.

Still another objective of the present invention is to provide ω-hydroxy fatty acid represented by Chemical Formula 1, which is prepared by the above method.

BRIEF DESCRIPTION OF THE DRAWINGS

FIG. 1a is a schematic diagram showing the sequential steps of reactions of producing medium-chain ω-hydroxy fatty acid (C9 ω-hydroxynonanoic acid) from long-chain fatty acid (C18 oleic acid) using hydratase, alcohol dehydrogenase, BVMO and ester hydrolase;

FIG. 1b is a schematic diagram showing the sequential steps of reactions of producing medium-chain ω-hydroxy fatty acid (C11 ω-hydroxyundec-9-enoic acid) from long-chain fatty acid (C18 ricinoleic acid) using alcohol dehydrogenase, BVMO and ester hydrolase;

FIG. 1c is a schematic diagram showing the sequential steps of reactions of producing ω-hydroxy fatty acid (C13

ω-hydroxytridec-11-enoic acid) from long-chain fatty acid (C20 lesquerolic acid) using alcohol dehydrogenase, BVMO and ester hydrolase;

FIG. 1d is a schematic diagram showing the sequential steps of reactions of producing α,ω-dicarboxylic acid (C10 α,ω-decanedioic acid) and octanol from long-chain fatty acid (C18 oleic acid) using hydratase, alcohol dehydrogenase, BVMO and ester hydrolase;

FIG. 1e is a schematic diagram showing the sequential steps of reactions of producing α,ω-dicarboxylic acid (C9 α,ω-nonanedioic acid) from long-chain fatty acid (C18 oleic acid) using hydratase, *Micrococcus luteus*-derived alcohol dehydrogenase, BVMO, ester hydrolase and *Pseudomonas putida*-derived alcohol dehydrogenase;

FIG. 1f is a schematic diagram showing the sequential steps of reactions of producing ω-amino fatty acid (C9 ω-aminononanoic acid) from long-chain fatty acid (C18 oleic acid) using hydratase, *Micrococcus luteus*-derived alcohol dehydrogenase, BVMO, ester hydrolase, *Pseudomonas putida*-derived alcohol dehydrogenase, and aminotransferase;

FIGS. 2a and 2b is show the production change over time of fatty acid having an ester group introduced into the chain thereof, which is produced from oleic acid using a transformant expressing oleic acid hydratase, alcohol dehydrogenase and BVMO of the present invention (FIG. 2a), and a graph showing the results of GC/MS analysis of hydrolysis products of ester (FIG. 2b);

FIGS. 3a and 3b show the production change over time of fatty acid having an ester group introduced into the chain thereof, which is produced from ricinoleic acid using a transformant expressing alcohol dehydrogenase and BVMO of the present invention (FIG. 3a), and a graph showing the results of GC/MS analysis of hydrolysis products of ester (FIG. 3b);

FIG. 4 shows the results of GC/MS analysis of products, resulting from the reaction of ester hydrolase with fatty acid having an ester group introduced into the chain thereof, which is produced from lesquerolic acid using a transformant expressing alcohol dehydrogenase and BVMO of the present invention;

FIGS. 5a and 5b show the production change over time of fatty acid having an ester group introduced into the chain thereof, which is produced from oleic acid using a transformant expressing oleic acid hydratase, alcohol dehydrogenase and BVMO of the present invention (FIG. 5a), and a graph showing the results of GC/IS analysis of hydrolysis products (sebacic acid) of ester (FIG. 5b);

FIG. 6 is a graph showing the production amount over time of reaction products, resulting from addition of a transformant expressing ester hydrolase and *Pseudomonas putida*-derived alcohol dehydrogenase to fatty acid having an ester group introduced into the chain thereof, which is produced from oleic acid using a transformant expressing oleic acid hydratase, *Micrococcus luteus*-derived alcohol dehydrogenase and BVMO of the present invention;

FIG. 7 is a graph showing the production change over time of α,ω-undec-2-enedioic acid (cis-2-undecene-1,11-dioic acid, which is produced from ricinoleic acid using a transformant expressing oleic acid hydratase, *Micrococcus luteus*-derived alcohol dehydrogenase, BVMO and ester hydrolase, *Pseudomonas putida*-derived alcohol dehydrogenase; and FIG. 8 is a graph showing the production amount over time of reaction products, resulting from addition of a transformant expressing ester hydrolase, *Pseudomonas putida*-derived alcohol dehydrogenase, and aminotransferase to fatty acid having an ester group introduced into the chain thereof, which is produced from oleic acid using a transformant expressing oleic acid hydratase, *Micrococcus luteus*-derived alcohol dehydrogenase and BVMO of the present invention.

DETAILED DESCRIPTION OF THE PREFERRED EMBODIMENTS

In one aspect to achieve the above objects, the present invention provides a transformant which is introduced with BVMO (Baeyer-Villiger monooxygenase) gene.

The term "BVMO (Baeyer-Villiger monooxygenase)", as used herein, refers to a monooxygenase which catalyzes various oxidation react ions, including a Baeyer-Villiger oxidation of producing a lactone or an ester compound by oxidation of a ketone. With respect to the objects of the present invention, as long as BVMO is expressed in the transformant and is capable of catalyzing the reaction of producing a fatty acid derivative having an ester group introduced into the chain thereof from keto fatty acid (e.g., 10-(octyloxy)-10-oxodecanoic acid from 10-ketostearic acid), the BVMO may be, but is not particularly limited to, preferably BVMO derived from a microorganism such as *Pseudomonas* sp. strain, *Rhodococcus* sp. strain, *Brevibacterium* sp. strain, *Comanonas* sp. strain, *Acinetobacter* sp. strain, *Arthrobacter* sp. strain, *Brachymonas* sp. strain, etc, more preferably, BVMO derived from *Pseudomonas putida*, *Pseudomonas fluorescens*, *Pseudomonas veronii*, *Rhodococcus jostii*, or *Pseudomonas* sp. strain HI-70, and most preferably, BVMO derived from *Pseudomonas putida*. The nucleotide sequence of the BVMO-encoding gene can be obtained from the known database such as GenBank at NCBI, and exemplified by a gene represented by GenBank Accession No. CAFK01000010, a gene obtained from an expression vector pJOE-KT2440BVMO (*Biotechnol. Lett.*, 29:1393-1398, 2007) which was prepared for BVMO gene expression, etc., and preferably, a polynucleotide sequence capable of encoding an amino acid sequence of SEQ ID NO. 9, etc.

Furthermore, the substitution, deletion, insertion, addition or inversion of one amino acid or several amino acids (may vary depending on positions of amino acid residues in the three-dimensional structure of the protein and types of the amino acid residues, specifically 2 to 20, preferably 2 to 10, more preferably 2 to 5 amino acids) may be included at one or more positions of amino acid sequence of BVMO, as long as the sequence is able to express BVMO having the ability to catalyze the reaction of producing a fatty acid derivative having an ester group introduced into the chain thereof from keto fatty acid in the transformant. As long as it is able to maintain or enhance the BVMO activity, an amino acid sequence having 80% or more, preferably 90% or more, more preferably 95% or more, even more preferably 97% or more homology with the amino acid sequence of BVMO may be included. Since the amino acid sequence of the enzyme showing the activity of the polypeptide may differ depending on the species or the strain of the microorganism, the substitution, deletion, insertion, addition or inversion of the amino acid also includes a naturally occurring mutated sequence or an artificially mutated sequence if it is based on the difference between individuals or between different species of the microorganism having the BVMO activity, but is not particularly limited thereto.

The term "homology", as used herein, refers to identity between two different amino acid sequences or two different nucleotide sequences, and can be determined by a method well known to those skilled in the art, for example, BLAST 2.0, which calculates parameters such as score, identity, and similarity, but is not particularly limited thereto.

The term "transformant", as used herein, refers to a cell or a microorganism which is mutated to express a desired protein after introduction of a polynucleotide encoding the desired protein into a host by a vector. In this regard, the polynucleotide to be introduced into the host cell may have any form, as long as it can be introduced into the host cell and expressed therein.

The transformant provided in the present invention may be prepared by introducing an expression vector harboring the known BVMO-encoding polynucleotide sequence or a known expression vector pJOE-KT2440BVMO (*Biotechnol. Lett.*, 29:1393-1398, 2007) into a host cell. In this regard, the host cell to be used is not particularly limited, as long as it is introduced with the polynucleotide sequence encoding the BVMO of the present invention, thereby expressing the BVMO. Preferably, the host cell may be a culturable unicellular prokaryotic or eukaryotic cell which is suitable for a biotransformation process, and more preferably, *E. coli*, yeast, or the like, and most preferably, *E. coli* BL21(DE3) cell.

The transformant of the present invention may be used for the production of C5 to C14 medium-chain ω-hydroxy fatty acids, α,ω-dicarboxylic acids, and ω-amino fatty acids by cleavage of C16 to C20 long-chain fatty acids contained in a medium. To this end, in addition to the gene encoding BVMO, a gene encoding hydratase or lipoxygenase, a gene encoding alcohol dehydrogenase, a gene encoding ester hydrolase (esterase), and a gene encoding aminotransferase may be further introduced.

The term "hydratase", as used herein, refers to an enzyme that reversibly produces a hydroxyl compound by adding water to a carbon double bond, and also called dehydratase because it catalyzes removal of water from the hydroxyl compound by a reverse reaction. The hydratase may be preferably derived from a strain such as *Stenotrophomonas maltophilia, Lysinibacillus fusiformis, Macrococcus caseolyticus, Propionibacterium acnes*, etc., but it is not particularly limited thereto. With respect to the objects of the present invention, the hydratase may be used for the purpose of producing a hydroxy fatty acid by adding a hydroxyl group to a C16 to C20 long-chain fatty acid.

The term "lipoxygenase", as used herein, refers to an oxygenase that adds molecular oxygen to unsaturated fatty acids, and an enzyme that produces hydroperoxide by recognizing a cis, cis-1,4-pentadiene structure of unsaturated fatty acid for stereospecific abstraction of a hydrogen atom from methylene and antarafacial oxygen insertion. With respect to the objectives of the present invention, the lipoxygenase may be used for the purpose of producing a hydroxy fatty acid by adding a hydroxyl group to a C16 to C20 long-chain fatty acid, like the above described hydratase.

The term "alcohol dehydrogenase", as used herein, means an enzyme that catalyzes a reaction of removing hydrogen from alcohol to produce aldehyde, ketone or carboxylic acid. The alcohol dehydrogenase may be preferably derived from *Micrococcus luteus, Pseudomonas* sp. strain, but it is not particularly limited thereto. With respect to the objects of the present invention, the alcohol dehydrogenase can be used for the purpose of producing keto fatty acid by removing hydrogens from hydroxy fatty acid which is produced by hydratase or lipoxygenase, or producing ω-oxofatty acid or α,ω-dicarboxylic acid from ω-hydroxy fatty acid which is produced by ester hydrolase.

The term "ester hydrolase (esterase)", as used herein, refers to an enzyme that hydrolyzes an ester bond of an ester compound. With respect to the objects of the present invention, the ester hydrolase may be used for the purpose of cleaving an ester group of a fatty acid derivative having the ester group introduced into the chain thereof, which is produced by BVMO.

The term "aminotransferase", as used herein, refers to an enzyme that converts an oxo group of ω-oxofatty acid into an amino group. The aminotransferase may be derived from a microorganism, but it is not particularly limited to, preferably, a strain such as *Chromobacterium violaceum, Silicibacter pomeroyi, Rhodococcus sphaeroides, Mesorhizobium lotimaff, Silicibacter* sp., etc. With respect to the objectives of the present invention, the aminotransferase can be used for the purpose of producing ω-amino fatty acid from ω-oxofatty acid produced by alcohol dehydrogenase, and preferably, used for the purpose of producing ω-amino fatty acid from C9, C11, C12 and C13 ω-oxofatty acids.

According to one embodiment of the present invention, a pACYC/oleic acid hydratase/alcohol dehydrogenase-expressing vector including the oleic acid hydratase gene derived from *Stenotrophomonas maltophilia* and the alcohol dehydrogenase gene derived from *Micrococcus luteus* was introduced into *E. coli* BL21(DE3) strain to prepare a primary transformant expressing hydratase and alcohol dehydrogenase, and pJOE-KT2440BVMO which is a vector expressing the BVMO gene derived from *Pseudomonas putida* was introduced into the primary transformant to prepare a secondary transformant capable of expressing oleic acid hydratase, alcohol dehydrogenase and BVMO at the same time (Example 1).

In another aspect to achieve the above objectives, the present invention provides a method for producing various degradation products from long-chain fatty acids by biotransformation using the transformant.

Specifically, the method for producing degradation products from long-chain fatty acids of the present invention includes the steps of (a) reacting long-chain fatty acid with the transformant which is introduced with the BVMO-encoding gene to obtain reactants; and (b) recovering degradation products from the reactants. In this regard, the degradation products may be medium-chain ω-hydroxy fatty acid, α-ω-dicarboxylic acid, ω-amino fatty acid or alcohol. Preferably, the degradation products may be C5 to C14 medium-chain ω-hydroxy fatty acid, α-ω-dicarboxylic acid, ω-amino fatty acid or C2 to C14 normal alcohol, more preferably, ω-hydroxynonanoic acid, ω-hydroxyundec-9-enoic acid, ω-hydroxytridec-11-enoic acid, α,ω-nonanedioic acid(azelaic acid), α,ω-decanedioic acid (sebacic acid), ω-aminononanoic acid, heptanoic acid, nonanoic acid, ω-hydroxyundecanoic acid, ω-hydroxytridecanoic acid, α,ω-undec-2-enedioic acid, ω-undecene-1,11-dioic acid), ω-aminoundec-9-enoic acid, α,ω-tridec-2-enedioic acid, normal octanol, etc.

In this regard the long-chain fatty acid may be, but is not particularly limited to, preferably C16 to C20 straight-chain fatty acid, and more preferably, oleic acid, ricinoleic acid, 12-hydroxystearic acid, linoleic acid, palmitoleic acid, lesquerolic acid, etc.

Further, the above reaction means an enzymatic reaction which catalyzes cleavage and degradation of the long-chain fatty acid or transfer of an amino group by reacting the long-chain fatty acid used as a substrate with various enzymes produced by the transformant, such as hydratase, lipoxygenase, alcohol dehydrogenase, ester hydrolase, aminotransferase. A series of the enzymes produced by the transformant are produced within the transformant, and the produced enzymes are secreted out from the transformant. Therefore, the reaction may occur within or outside the transformant. For example, while the transformant is cultured in a medium containing a carbon source, long-chain fatty acids are added to the medium after a predetermined amount of the carbon source in the medium is consumed, and cleavage and degradation of the long-chain fatty acid or transfer of an amino group is catalyzed by the enzymes produced from the transformant, thereby producing various degradation products; the transformant is added to a reaction buffer solution containing long-chain fatty acid, and cleavage and degradation of the long-chain fatty acid or transfer of an amino group is catalyzed, thereby producing various degradation products; or each of the enzymes is separated from the transformant, and the separated enzymes are immobilized onto supports, respectively and then they are added to the reaction buffer solution containing long-chain fatty acid, and the cleavage or degradation of the long-chain fatty acid is catalyzed by the immobilized enzymes, thereby producing various degradation products. In this regard, the content of long-chain fatty acid in the medium or the buffer solution may be, but is not particularly limited to, preferably added to a final concentration of 0.1 to 100 g/L.

The term "culture", as used herein, refers to culturing of a microorganism under artificially controlled environmental conditions. In the present invention, the method for culturing the transformant may be conducted using a method widely known in the art. Specifically, examples of the culturing method include a batch process, a fed batch or repeated fed batch process in a continuous manner, but are not limited thereto.

The medium used for the culture should comply with the requirements of a specific strain in a proper manner while controlling temperature, pH, etc., under aerobic conditions in a typical medium containing a proper carbon source, nitrogen source, amino acids, vitamins, etc. Carbon sources to be used may include sugars such as glucose, sucrose, and lactose, lipids, fatty acids, glycerol. These materials may be used separately or in combination. Nitrogen sources to be used may include inorganic nitrogen sources such as ammonia, ammonium sulfate, ammonium chloride, and ammonium phosphate; and organic nitrogen sources such as amino acids including glutamic acid, peptone, meat extract, yeast extract, malt extract, corn steep liquor, casein hydrolysates, etc. These nitrogen sources may be used separately or in combination. In order to maintain aerobic condition, oxygen or oxygen-containing gas (e.g., air) is introduced into the culture broth. The temperature of the culture broth is normally 15° C. to 37° C., preferably 20° C. to 30° C., and the culture is conducted for 10 to 100 hours.

Furthermore, the step of recovering the degradation products such as medium-chain ω-hydroxy fatty acid, α,ω-dicarboxylic acid, ω-amino fatty acid, alcohol from the reaction solution may be performed by a method known in the art, such as dialysis, centrifugation, filtration, solvent extraction, chromatography, crystallization, etc. For example, the supernatant obtained after removing the transformant by centrifugation of the reaction solution, may be applied to a solvent extraction to recover the desired degradation products. Otherwise, any method may be used without limitation, as long as the degradation products are recovered by combinations of the known experimental methods suitable for the properties of each degradation product.

When the hydratase-encoding gene, alcohol dehydrogenase-encoding gene, BVMO-encoding gene, ester hydrolase-encoding gene, and aminotransferase-encoding gene provided in the present invention are introduced into a host cell in different combinations, various transformants having different functions can be prepared, and each of the transformants prepared is able to produce C5 to C14 medium-chain ω-hydroxy fatty acids, α,ω-dicarboxylic acids, ω-amino fatty acids or alcohols from C16 to C20 long-chain fatty acids (oleic acid, ricinoleic acid, linoleic acid, lesquerolic acid, etc.) present in the medium or reaction solution.

For example, a transformant prepared by introducing the alcohol dehydrogenase-encoding gene and the BVMO-encoding gene into $E.\ coli$ is able to convert a long-chain fatty acid into a long-chain fatty acid having an ester group which is introduced into the chain thereof. When the transformant further includes ester hydrolase, alcohol dehydrogenase or aminotransferase individually or in combination, the long-chain fatty acid having an ester group introduced into the chain thereof can be converted into various types of medium-chain o-hydroxy fatty acids, α,ω-dicarboxylic acids, e-amino fatty acids or alcohols.

In one embodiment of the present invention, the transformant capable of expressing hydratase, alcohol dehydrogenase, BVMO and ester hydrolase can produce medium-chain ω-hydroxy fatty acids such as ω-hydroxynonanoic acid (C9) from long-chain fatty acids such as oleic acid (C18), in which hydratase converts long-chain fatty acids into hydroxy fatty acids, alcohol dehydrogenase produces keto fatty acids by removing hydrogens from the converted hydroxy fatty acids, BVMO oxidizes the produced keto fatty acids to produce long-chain fatty acids having an ester group introduced into the chain thereof, and ester hydrolase hydrolyzes an ester bond of the produced long-chain fatty acids having an ester group introduced into the chain thereof, thereby producing medium-chain ω-hydroxy fatty acids (FIG. 1a).

In another embodiment of the present invention, the transformant capable of expressing alcohol dehydrogenase, BVMO and ester hydrolase can produce medium-chain ω-hydroxy fatty acids such as ω-hydroxyundec-9-enoic acid (C11) from hydroxy long-chain fatty acids such as ricinoleic acid (C18), in which alcohol dehydrogenase produces keto fatty acids by removing hydrogens from hydroxy long-chain fatty acids, BVMO oxidizes the produced keto fatty acids to produce long-chain fatty acids having an ester group introduced into the chain thereof, and ester hydrolase hydrolyzes an ester bond of the produced long-chain fatty acids having an ester group which is introduced into the chain thereof, thereby producing medium-chain ω-hydroxy fatty acids (FIG. 1b).

In still another embodiment of the present invention, the transformant capable of expressing alcohol dehydrogenase, BVMO and ester hydrolase can produce medium-chain ω-hydroxy fatty acids such as ω-hydroxytridec-11-enoic acid (C13) from hydroxy long-chain fatty acids such as lesquerolic acid (C20), in which alcohol dehydrogenase produces keto fatty acids by removing hydrogens from hydroxy long-chain fatty acids, BVMO oxidizes the produced keto fatty acids to produce long-chain fatty acids having an ester group introduced into the chain thereof, and ester hydrolase hydrolyzes an ester bond of the produced long-chain fatty acids having an ester group which is introduced into the chain thereof, thereby producing medium-chain ω-hydroxy fatty acids (FIG. 1c).

In still another embodiment of the present invention, the transformant capable of expressing hydratase, alcohol dehydrogenase, BVMO and ester hydrolase can produce, α,ω- dicarboxylic acid such as α,ω-decanedioic acid (C10) and octanol (C8) from long-chain fatty acids such as oleic acid (C18), in which hydratase converts long-chain fatty acids into hydroxy fatty acids, alcohol dehydrogenase produces keto fatty acids by removing hydrogens from the converted hydroxy fatty acids, BVMO oxidizes the produced keto fatty acids to produce long-chain fatty acids having an ester group introduced into the chain thereof, and ester hydrolase hydrolyzes an ester bond of the produced long-chain fatty acids having an ester group introduced into the chain thereof, thereby producing α,ω-dicarboxylic acid and alcohol (FIG. 1d).

In still another embodiment of the present invention, the transformant capable of expressing hydratase, *Micrococcus luteus*-derived alcohol dehydrogenase, BVMO, ester hydrolase, and *Pseudomonas putida*-derived alcohol dehydrogenase can produce α,ω-dicarboxylic acids such as α,ω-nonanedioic acid (C9) from long-chain fatty acids such as oleic acid (C18), in which hydratase converts long-chain fatty acids into hydroxy fatty acids, *Micrococcus luteus*-derived alcohol dehydrogenase produces keto fatty acids by removing hydrogens from the converted hydroxy fatty acids, BVMO oxidizes the produced keto fatty acids to produce long-chain fatty acids having an ester group introduced into the chain thereof, ester hydrolase hydrolyzes an ester bond of the produced long-chain fatty acids having an ester group introduced into the chain thereof, thereby producing ω-hydroxy fatty acids, and *Pseudomonas putida*-derived alcohol dehydrogenase produces α,ω-dicarboxylic acids by removing hydrogens from the ω-hydroxy fatty acids (FIG. 1e).

In still another embodiment of the present invention, the transformant capable of expressing hydratase, *Micrococcus luteus*-derived alcohol dehydrogenase, BVMO, ester hydrolase, *Pseudomonas putida*-derived alcohol dehydrogenase and aminotransferase can produce ω-amino fatty acids such as ω-aminononanoic acid (C9) from long-chain fatty acids such as oleic acid (C18), in which hydratase converts long-chain fatty acids into hydroxy fatty acids, *Micrococcus luteus*-derived alcohol dehydrogenase produces keto fatty acids by removing hydrogens from the converted hydroxy fatty acids, BVMO oxidizes the produced keto fatty acids to produce long-chain fatty acids having an ester group introduced into the chain thereof, ester hydrolase hydrolyzes an ester bond of the produced long-chain fatty acids having an ester group introduced into the chain thereof, thereby producing ω-hydroxy fatty acids, *Pseudomonas putida*-derived alcohol dehydrogenase produces ω-keto fatty acids by removing hydrogens from the ω-hydroxy fatty acids, and aminotransferase transfers amino groups to the produced ω-keto fatty acid, thereby producing ω-amino fatty acids (FIG. 1f).

Meanwhile, ω-hydroxy fatty acids produced from long-chain fatty acids can be converted into α,ω-dicarboxylic acids by *Pseudomonas putida*-derived alcohol dehydrogenase (Examples 5 and 6), or into ω-amino fatty acids by successive reaction with aminotransferase (Example 7).

C5 to C14 ω-hydroxy fatty acids, α,ω-dicarboxylic acids, ω-amino fatty acids, and alcohols produced by the transformants are secreted into the medium or reaction buffer solution. Therefore, when the transformant is immobilized on an immobilization support or the transformant is cultured in a fed-batch or continuous mode, C5 to C14 ω-hydroxy fatty acids, α,ω-dicarboxylic acids, ω-amino fatty acids and alcohols can be produced in large amount.

According to one embodiment of the present invention, *Stenotrophomonas maltophilia*-derived oleic acid hydratase gene and *Micrococcus luteus*-derived alcohol dehydrogenase gene were introduced into *E. coli* BL21(DE3) to prepare a transformant expressing hydratase and alcohol dehydrogenase, and *Pseudomonas fluorescens*-derived BVMO gene was introduced into the transformant to prepare a transformant expressing hydratase, alcohol dehydrogenase and BVMO (Example 4). Further, the transformant expressing hydratase, alcohol dehydrogenase, BVMO was cultured and reacted with oleic acid. As a result, 10-hydroxy stearic acid, 10-keto stearic acid, and fatty acid having an ester group which is introduced into the chain thereof were produced (FIG. 5), and *Pseudomonas fluorescens*-derived ester hydrolase was added thereto, thereby producing α,ω-decanedioic acid and octanol.

In still another aspect to achieve the above objects, the present invention provides a novel ω-hydroxy fatty acid represented by the following Chemical Formula 1, which is prepared by the above method.

[Chemical Formula 1]

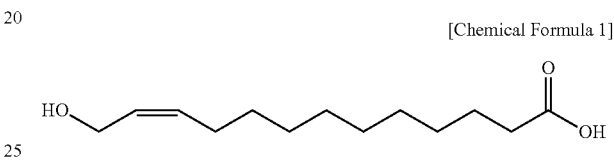

The above compound can be prepared by the above described method. For example, the transformant expressing oleic acid hydratase, alcohol dehydrogenase and BVMO is cultured, and then reacted with lesquerolic acid to produce fatty acid having an ester group introduced into the chain thereof, and *Pseudomonas fluorescens*-derived ester hydrolase is added to and reacted with the produced fatty acid having an ester group introduced into the chain thereof, thereby producing the novel ω-hydroxy fatty acid of Chemical Formula I. The novel ω-hydroxy fatty acid thus produced can be analyzed by GC/MS to examine its structure.

In still another aspect to achieve the above objects, the present invention provides a method for producing a fatty acid derivative having an ester group introduced into the chain thereof from keto fatty acid using BVMO.

Hereinafter, the present invention will be described in more detail with reference to Examples. However, these Examples are for illustrative purposes only, and the invention is not intended to be limited by these Examples.

Example 1

Production of ω-Hydroxynonanoic Acid by Multi-Step Enzymatic Synthesis

1) Gene Cloning

To prepare a recombinant expression vector including oleic acid hydratase and alcohol dehydrogenase genes, *Stenotrophomonas maltophilia*-derived oleic acid hydratase gene and *Micrococcus luteus*-derived alcohol dehydrogenase gene were cloned.

First, oleic acid hydratase gene was amplified by PCR using a plasmid vector pET 28(+)a/oleic acid hydratase (J. Biotechnol., 153:17-23, 2012) as a template and primers (SEQ ID NOS: 1 and 2) which were prepared by including PvuI and XhoI restriction enzyme sites.

Forward primer:

(SEQ ID NO: 1)
5'-gctagcatgtattacagtaatggtaactatgaa-3'

-continued

```
Reverse primer:
                                    (SEQ ID NO: 2)
5'-ggctcgagctatattagtttactttctttca-3'
```

The amplified PCR product was digested with restriction enzymes PvuI and XhoI, and inserted into a plasmid vector pACYC (manufactured by Novagen) to prepare a pACYC/oleic acid hydratase expression vector.

Further, alcohol dehydrogenase was amplified by PCR using DNA sequence (Genebank Accession No. ZP_07049769) of *Micrococcus luteus*-derived alcohol dehydrogenase as a template and primers (SEQ ID NOS: 3 and 4) which were prepared by including EcoRI and HindIII restriction enzyme sites.

```
Forward primer:
                                    (SEQ ID NO: 3)
5'-atcgaattcgtccgagttcacccgtttcga-3'

Reverse primer:
                                    (SEQ ID NO: 4)
5'-atatcaagcttcagccgagcggggtgtcct-3'
```

The amplified PCR product was digested with restriction enzymes EcoRI and HindIII, and inserted into the prepared pACYC/oleic acid hydratase expression vector to prepare a pACYC/oleic acid hydratase/alcohol dehydrogenase expression vector.

2) Host Cell Culture

To maintain the plasmid, *E. coli* BL21(DE3) was cultured in a Riesenberg medium containing 10 g/l glucose and an appropriate antibiotic. At this time, the Riesenberg medium contained 4 g/l $N(NH_4)_2HPO_4$, 13.5 g/l $KH_2PO_4$, 1.7 g/l citric acid, 1.4 g/l $MgSO_4$ and 10 ml/l trace metal solution (10 g/l $FeSO_4$, 2.25 g/l $ZnSO_4$, 1.0 g/l $CuSO_4$, 0.5 g/l $MnSO_4$, 0.23 g/l $Na_2B_4O_7$, 2.0 g/l $CaCl_2$ and 0.1 g/l $(NH_4)_6Mo_7O_{24}$), and *Micrococcus luteus* was cultured in LB medium.

3) Production of ω-Hydroxynonanoic Acid by Transformant

First, the pACYC/oleic acid hydratase/alcohol dehydrogenase expression vector of Example 1-1), to which *Stenotrophomonas maltophilia*-derived oleic acid hydratase gene and *Micrococcus luteus*-derived alcohol dehydrogenase genes were inserted, was introduced into *E. coli* BL21(DE3) strain cultured in Example 1-2) to prepare a primary transformant.

Next, the primary transformant was introduced with the expression vector pJOE-KT2440BVMO (Biotechnol. Lett., 29:1393-1398, 2007) which was prepared to express *Pseudomonas putida*-derived BVMO gene, thereby preparing a secondary transformant capable of expressing oleic acid hydratase, alcohol dehydrogenase and BVMO.

Subsequently, while the secondary transformant was cultured in a Riesenberg mineral medium at 30° C. an rd 200 rpm, it was treated with IPTG and rhamnose to express oleic acid hydratase, alcohol dehydrogenase and BVMO, and reacted with 1 mM oleic acid to produce ω-hydroxynonanoic acid (FIG. 2). FIG. 2a is a graph showing the production change over time of fatty acid having an ester group introduced into the chain thereof, which was produced by using the secondary transformant, in which (•) indicates the concentration of oleic acid, (Δ) indicates the concentration of 10-hydroxystearic acid, (▽) indicates the concentration of 10-ketostearic acid, (■) indicates the concentration of fatty acid having an ester group introduced into the chain thereof, and (▲) indicates the concentration of ω-hydroxynonanoic acid. FIG. 2b shows the results of GC/MS analysis of reaction products which were treated with ester hydrolase after termination of the reaction. Most of the fatty acid having an ester group introduced into the chain thereof which was prepared from oleic acid was converted into n-nonanoic acid and ω-hydroxynonanoic acid.

Example 2

Production of ω-Hydroxyundec-9-Enoic Acid from Ricinoleic Acid

ω-hydroxyundec-9-enoic acid was produced from the substrate ricinoleic acid using the transformant which was prepared in Example 1.

That is, ω-hydroxyundec-9-enoic acid was produced in the same manner as in Example 1-3), except that 1 mM ricinoleic acid was added instead of oleic acid (FIG. 3). FIG. 3a is a graph showing the production change over time of fatty acid having an ester group introduced into the chain thereof, which was produced from ricinoleic acid by using the transformant, in which (Δ) indicates the concentration of ricinoleic acid, (▽) indicates the concentration of 12-ketooleic acid, (■) indicates the concentration of fatty acid having an ester group introduced into the chain thereof, and (▲) indicates the concentration of ω-hydroxyundec-9-enoic acid. FIG. 3b shows the results of GC/MS analysis of reaction products which were treated with ester hydrolase after termination of the reaction. Most of the fatty acid having an ester group introduced into the chain thereof, which was prepared from ricinoleic acid, was converted into n-heptanoic acid and ω-hydroxyundec-9-enoic acid.

Example 3

Production of ω-Hydroxytridec-11-Enoic Acid from Lesquerolic Acid

ω-hydroxytridec-11-enoic acid was produced from the substrate lesquerolic acid using the transformant prepared in Example 1.

That is, ω-hydroxytridec-11-enoic acid was produced in the same manner as in Example 1-3), except that 1 mM lesquerolic acid was added instead of oleic acid (FIG. 4). FIG. 4 shows the results of GC/MS analysis of reaction products, after production of ω-hydroxytridec-11-enoic acid from lesquerolic acid using the transformant and ester hydrolase. Most of lesquerolic acid was converted into heptanoic acid and ω-hydroxytridec-11-enoic acid.

Example 4

Production of α,ω-Decanedioic Acid from Oleic Acid pACYC/oleic acid hydratase/alcohol dehydrogenase expression vector prepared in Example 1 and *Pseudomonas fluorescens*-derived BVMO gene expression vector (*Appl. Microbiol. Biotechnol.* 73:1065-1072, 2007) were introduced into *E. coli* BL21(DE3) strain to prepare a transformant, which was used to produce α,ω-decanedioic acid (sebacic acid) from the substrate oleic acid (FIG. 5). FIG. 5a is a graph showing the production change over time of fatty acid having an ester group introduced into the chain thereof, which was produced by using the above transformant, in which (•) indicates the concentration of oleic acid, (Δ)

indicates the concentration of 10-hydroxystearic acid, (▽) indicates the concentration of 10-ketostearic acid, and (■) indicates the concentration of fatty acid having an ester group introduced into the chain thereof. FIG. 5b shows the results of GC/MS analysis of reaction products which were treated with ester hydrolase after termination of the reaction. Most of the fatty acid having an ester group introduced into the chain thereof, which was prepared from oleic acid, was converted into sebacic acid and normal octanol.

Example 5

Production of α,ω-Nonanedioic Acid from Oleic Acid

1) Gene Cloning

To prepare a recombinant expression vector including ester hydrolase and alcohol dehydrogenase genes, *Pseudomonas fluorescens*-derived ester hydrolase gene and *Pseudomonas putida*-derived alcohol dehydrogenase gene were cloned.

First, ester hydrolase gene was amplified by PCR using a plasmid vector pGASTON/ester hydrolase (*Agric Biol. Chem.*, 54:2039-2045, 1990) as a template and primers (SEQ ID NOS: 5 and 6) which were prepared by including NdeI and XhoI restriction enzyme sites.

```
Forward primer:
                                     (SEQ ID NO:. 5)
5'-gcgccatatatgatgagcacatttgttgcaaaa-3'

Reverse primer:
                                     (SEQ ID NO: 6)
5'-gcgcctcgagtcagtggtgatggtgatgatgactccgccgccactt
t-3'
```

The amplified PCR product was digested with restriction enzymes NdeI and XhoI, and inserted into a plasmid vector pCOLAduet-1 (manufactured by Novagen) to prepare a pCOLAduet-1/ester hydrolase expression vector.

Further, alcohol dehydrogenase was amplified by PCR using DNA sequence (*J. Biotechnol.* 262:17712-17718, 1987) of *Pseudomonas putida*-derived alcohol dehydrogenase as a template and primers (SEQ ID NOS: 7 and 8) which were prepared by including BamHI and NotI restriction enzyme sites.

```
Forward primer:
                                     (SEQ ID NO: 7)
5'-gcgcggatccgatgtacgactatataatcgtt-3'

Reverse primer:
                                     (SEQ ID NO: 8)
5'-gcgcgcggccgcttagtggtgatggtgatgatgcatgcagacagct
at-3'
```

The amplified PCR product was digested with restriction enzymes BamI and NotI, and inserted into the prepared pCOLAduet-1/ester hydrolase expression vector to prepare a pCOLAduet-1/ester hydrolase/alcohol dehydrogenase expression vector.

2) Production of α,ω-Nonanedioic Acid by Transformant

First, the pCOLAduet-1/ester hydrolase/alcohol dehydrogenase expression vector of Example 5-1), to which *Pseudomonas fluorescens*-derived ester hydrolase and *Pseudomonas putida*-derived alcohol dehydrogenase genes were inserted, was introduced into *E. coli* BL21(DE3) strain cultured in Example 1-2) to prepare a transformant.

α,ω-nonanedioic acid (azelaic acid) was produced from the substrate oleic acid using the transformant prepared in Example 1 and the transformant prepared in Example 5-1). Fatty acid having an ester group introduced into the chain thereof was produced from oleic acid using the transformant prepared in Example 1, and azelaic acid was produced from the fatty acid having an ester group introduced into the chain thereof using the transformant prepared in Example 5-1) (FIG. 6). FIG. 6 is a graph showing the production change over time of azelaic acid produced, in which (■) indicates the concentration of fatty acid having an ester group introduced into the chain thereof, (▲) indicates the concentration of ω-hydroxynonanoic acid, (◇) indicates the concentration of 9-oxononanoic acid, and (♦) indicates the concentration of azelaic acid.

Example 6

Production of α,ω-Undec-2-Enedioic Acid from Ricinoleic Acid

*E. coli* BL21 (DE3) strain was introduced with the pACYC/oleic acid hydratase/alcohol dehydrogenase expression vector prepared in Example 1, *Pseudomonas putida*-derived BVMO gene expression vector, and the pCOLAduet-1/ester hydrolase/alcohol dehydrogenase expression vector prepared in Example 5-1) to prepare a transformant.

α,ω-undec-2-enedioic acid was produced from ricinoleic acid ($C_{18}H_{34}O_3$) using the transformant (FIG. 7). FIG. 7 is a graph showing the production change over time of α,ω-undec-2-enedioic acid which was produced from ricinoleic acid using the above transformant, in which (Δ) indicates the concentration of ricinoleic acid, (▽) indicates the concentration of 12-ketooleic acid, (■) indicates the concentration of fatty acid having an ester group introduced into the chain thereof, (▲) indicates the concentration of ω-hydroxyundec-9-enoic acid, (◇) indicates the concentration of 9-oxoundec-9-enoic acid, and (♦) indicates the concentration of α,ω-undec-2-enedioic acid.

Meanwhile, heptanoic acid and α,ω-tridec-2-enedioic acid could be produced from lesquerolic acid by using the above transformant.

Example 7

Production of α-Aminononanoic Acid from Oleic Acid

1) Preparation of Transformant

First, the pCOLAduet-1/ester hydrolase/alcohol dehydrogenase expression vector of Example 5-1), to which *Pseudomonas fluorescens*-derived ester hydrolase and *Pseudomonas putida*-derived alcohol dehydrogenase genes were inserted, was introduced into *E. coli* to prepare a primary transformant.

Next, Silicibacter-derived aminotransferase expression vector (*ChemCatchem*, 5:154-157, 2013) was introduced into the primary transformant to prepare a secondary transformant capable of expressing ester hydrolase, alcohol dehydrogenase and aminotransferase.

2) Production of α-Aminononanoic Acid by Transformant

α-aminononanoic acid was produced from the substrate oleic acid using the transformant prepared in Example 1 and the secondary transformant prepared in Example 6-1). Fatty acid having an ester group introduced into the chain thereof was produced from oleic acid using the transformant prepared in Example 1, and α-aminononanoic acid was produced from the fatty acid having an ester group introduced into the chain thereof using the transformant prepared in Example 6-1) (FIG. 8). FIG. 8 is a graph showing the production change over time of α-aminononanoic acid produced, in which (■) indicates the concentration of fatty acid having an ester group introduced into the chain thereof, (▲) indicates the concentration of ω-hydroxy nonanoic acid, (◇) indicates the concentration of 9-oxononanoic acid, and (♦) indicates the concentration of α-aminononanoic acid.

Meanwhile, heptanoic acid and α-aminoundec-9-enoic acid could be produced from ricinoleic acid by using the transformant.

EFFECT OF THE INVENTION

Degradation products such as C5 to C14 ω-hydroxy fatty acids, α,ω-dicarboxylic acids, ω-amino fatty acids, alcohols can be produced in a large amount from C16 to C20 long-chain fatty acids contained in a medium by biotransformation using a transformant capable of expressing BVMO of the present invention. Therefore, it can be widely used to produce ω-hydroxy fatty acids, α,ω-dicarboxylic acids, ω-amino fatty acids or alcohols in a more safe and economic manner.

What is claimed is:

1. A transformant introduced with a hydratase-encoding gene, an alcohol dehydrogenase-encoding gene, a Baeyer-Villiger monooxygenase(BVMO)-encoding gene and an ester hydrolase-encoding gene,
   wherein the transformant has ability to produce medium-chain ω-hydroxy fatty acids, or α,ω-dicarboxylic acids from C16-C20 long-chain fatty acids; and
   wherein the BVMO-encoding gene is obtained *Pseudomonas fluorescens, Pseudomonas putida, Pseudomonas veronii, Rhodococcus jostii* or *Pseudomonas* sp. strain HI-70 and catalyzes Bayer-Villiger oxidation of producing a degradation product by oxidation of a ketone.

2. The transformant according to claim 1, wherein ω-hydroxynonanoic acid (C9) is produced as the medium-chain ω-hydroxy fatty acid, when oleic acid (C18) is used as the long-chain fatty acid.

3. The transformant according to claim 1, wherein α,ω-decanedioic acid (C10) is produced as the α,ω-dicarboxylic acid and octanol (C8) is produced as an alcohol, when oleic acid (C18) is used as the long-chain fatty acid.

4. A transformant introduced with an alcohol dehydrogenase-encoding gene, a Baeyer-Villiger monooxygenase (BVMO)-encoding gene and an ester hydrolase-encoding gene,
   wherein the transformant has ability to produce medium-chain ω-hydroxy fatty acid from C 16-C20 hydroxy long-chain fatty acids; and
   wherein the BVMO-encoding gene is obtained from *Pseudomonas fluorescens, Pseudomonas putida, Pseudomonas veronii, Rhodococcus josii* or *Pseudomonas* sp. strain HI-70 and catalyzes Bayer-Villiger oxidation of producing a degradation product by oxidation of a ketone.

5. The transformant according to claim 4, wherein ω-hydroxyundec-9-enoic acid (C11) is produced as the medium-chain ω-hydroxy fatty acid, when ricinoleic acid (C18) is used as the hydroxy long-chain fatty acid.

6. The transformant according to claim 4, wherein ω-hydroxytridec-11-enoic acid (C13) is produced as the medium-chain ω-hydroxy fatty acid, when lesquerolic acid (C20) is used as the hydroxy long-chain fatty acid.

7. A transformant introduced with a hydratase-encoding gene, two different alcohol dehydrogenases-encoding genes, a Baeyer-Villiger monooxygenase(BVMO)-encoding gene and an ester hydrolase-encoding gene,
   wherein the transformant has ability to produce α,ω-dicarboxylic acids from C16-C20 long-chain fatty acids; and
   wherein the BVMO-encoding gene is obtained from *Pseudomonas fluorescens, Pseudomonas putida, Pseudomonas veronii, Rhodococcus jostii* or *Pseudomonas* sp. strain HI-70 and catalyzes Bayer-Villiger oxidation of producing a degradation product by oxidation of a ketone.

8. The transformant according to claim 7, wherein α,ω-nonanedioic acid (C9) is produced as the α,ω-dicarboxylic acid, when oleic acid (C18) is used as the long -chain fatty acid.

9. A transformant introduced with a hydratase-encoding gene, two different alcohol dehydrogenases-encoding genes, a Baeyer-Villiger monooxygenase(BVMO)-encoding gene, an ester hydrolase-encoding gene, and an aminotransferase-encoding gene,
   wherein the transformant has ability to produce ω-amino fatty acids from C16-C20 long-chain fatty acids; and
   wherein the BVMO-encoding gene is obtained from *Pseudomonas fluorescens, Pseudomonas putida, Pseudomonas veronii, Rhodococcus jostii* or *Pseudomonas* sp. strain HI-70 and catalyzes Bayer-Villiger oxidation of producing a degradation product by oxidation of a ketone.

10. The transformant according to claim 9, wherein ω-aminononanoic acid (C9) is produced as the ω-amino fatty acid, when oleic acid (C18) is used as the long-chain fatty acid.

11. A method for producing degradation products from long-chain fatty acids, comprising
   (a) reacting the transformant of any one of claims 1 to 7, 8, 9 and 10 with the C16-C20 long-chain fatty acid to obtain reactants; and
   (b) recovering the degradation product from the reactants.

12. The method according to claim 11, wherein the long-chain fatty acid is oleic acid, ricinoleic acid, 12-hydroxystearic acid, linoleic acid, palmitoleic acid, lesquerolic acid or a combination thereof.

13. The method according to claim 11, wherein the degradation products are medium-chain ω-hydroxy fatty acids, α,ω-dicarboxylic acids, ω-amino fatty acids, alcohols or combinations thereof.

14. The method according to claim 11, wherein the degradation products are C5 to C14 medium-chain ω-hydroxy fatty acids, α,ω-dicarboxylic acids, ω-amino fatty acids, C2 to C14 normal alcohols or combinations thereof.

15. The method according to claim 11, wherein the degradation products are ω-hydroxynonanoic acid, ω-hydroxyundec-9-enoic acid, ω-hydroxytridec-11-enoic acid, α,ω-nonanedioic acid (azelaic acid), α,ω-decanedioic acid (sebacic acid), ω-aminononanoic acid, heptanoic acid, nonanoic acid, ω-hydroxyundecanoic acid, ω-hydroxytridecenoic acid, α,ω-undec-2-enedioic acid (cis-2-undecene-1, 11-dioic acid), normal octanol or a combination thereof.

* * * * *